(12) United States Patent
Dubois et al.

(10) Patent No.: US 9,536,056 B2
(45) Date of Patent: Jan. 3, 2017

(54) METHOD AND SYSTEM OF MACHINE-TO-MACHINE VERTICAL INTEGRATION WITH PUBLISHER SUBSCRIBER ARCHITECTURE

(71) Applicant: Verizon Patent and Licensing Inc., Basking Ridge, NJ (US)

(72) Inventors: Jean F Dubois, Boothbay Harbor, ME (US); Patrick J Moran, Shrewsbury, MA (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 545 days.

(21) Appl. No.: 14/015,462

(22) Filed: Aug. 30, 2013

(65) Prior Publication Data

US 2015/0066926 A1    Mar. 5, 2015

(51) Int. Cl.
*G06F 17/30* (2006.01)
*G06F 19/00* (2011.01)

(52) U.S. Cl.
CPC ....... *G06F 19/3481* (2013.01); *G06F 19/3406* (2013.01); *G06F 19/3418* (2013.01)

(58) Field of Classification Search
CPC .................................................. G06F 19/3406
USPC ....................................... 707/737; 455/414.1
See application file for complete search history.

(56) References Cited

U.S. PATENT DOCUMENTS

| | | | | |
|---|---|---|---|---|
| 2007/0038480 A1* | 2/2007 | Kay | ....................... | G06N 5/025 705/4 |
| 2007/0073836 A1* | 3/2007 | Choi | ..................... | H04L 67/125 709/217 |
| 2009/0023433 A1* | 1/2009 | Walley | .............. | H04M 1/72569 455/418 |
| 2010/0153133 A1* | 6/2010 | Angell | ................... | G06Q 50/24 705/3 |
| 2010/0153174 A1* | 6/2010 | Angell | ................... | G06Q 10/10 705/7.29 |
| 2010/0332288 A1* | 12/2010 | Higgins | ................ | G06Q 30/02 705/14.45 |
| 2015/0067176 A1* | 3/2015 | Dubois | .................. | H04L 69/08 709/227 |

\* cited by examiner

*Primary Examiner* — Baoquoc N To

(57) ABSTRACT

An approach for machine-to-machine vertical integration with publisher-subscriber architecture is provided. The approach includes dynamically registering a plurality of sensors associated with a plurality of subscribers. The sensors are monitored as part of a sensor platform to maintain sensor data for the plurality of subscribers. Also, the sensor data are acquired from the plurality of sensors as a collective data set to determine one or more trends. The collective data set is tagged with metadata for the determined trend.

24 Claims, 21 Drawing Sheets

800

METHOD AND SYSTEM OF MACHINE-TO-MACHINE VERTICAL INTEGRATION WITH PUBLISHER SUBSCRIBER ARCHITECTURE

BACKGROUND INFORMATION

Numerous sensor devices are capable of collecting and transferring sensor data over a network. These devices typically operate independently with little to no coordination among them. The widespread practice of data collection systems using unique data formats particular to the systems further contributes to the isolation of sensor devices. As such, service providers and users face challenges in taking advantage of sensor data aggregated into a collective set.

Based on the foregoing, there is a need for collecting and processing data from a multitude of sensor devices in an integrated manner.

BRIEF DESCRIPTION OF THE DRAWINGS

Various exemplary embodiments are illustrated by way of example, and not by way of limitation, in the figures of the accompanying drawings in which like reference numerals refer to similar elements and in which.

DESCRIPTION OF THE PREFERRED EMBODIMENT

An apparatus, method, and software for providing machine-to-machine vertical integration with publisher-subscriber architecture, is described. In the following description, for the purposes of explanation, numerous specific details are set forth in order to provide a thorough understanding of the present invention. It is apparent, however, to one skilled in the art that the present invention may be practiced without these specific details or with an equivalent arrangement. In other instances, well-known structures and devices are shown in block diagram form in order to avoid unnecessarily obscuring the present invention. Although the various exemplary embodiments are described with respect to a sensor platform, it is contemplated that these embodiments have applicability to other architectures.

Although the various exemplary embodiments are described with respect to cloud computing and services, it is contemplated these embodiments have applicability to other computing technologies and architectures.

Figure 1:
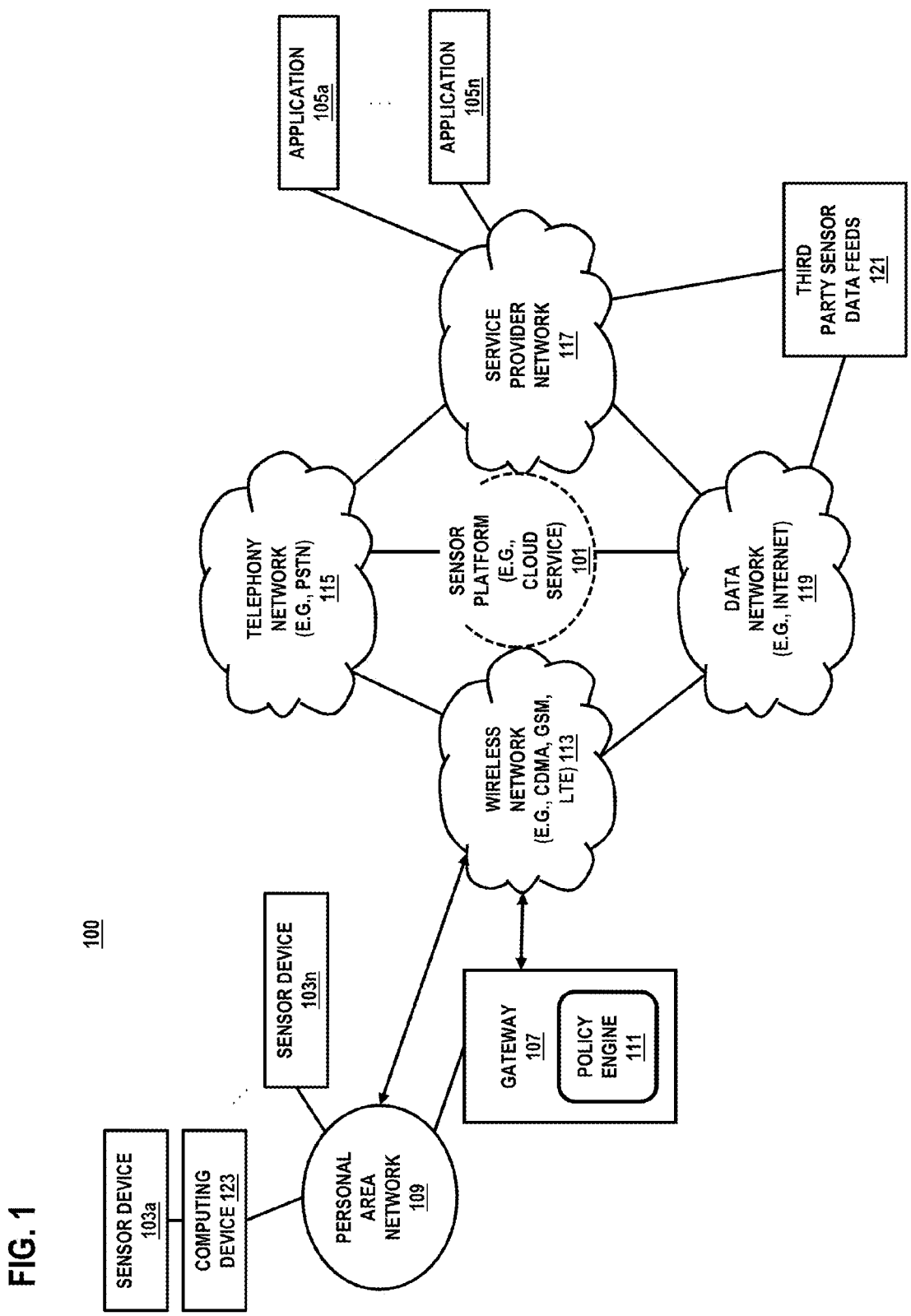
FIG. 1 is a diagram of a system capable of collecting data from various sensor devices into a unified system for immediate use by applications and analytics, according to one embodiment.

FIG. 1 is a diagram of a system capable of collecting data from various sensor devices into a unified system for immediate use by applications and analytics, according to one embodiment. For the purpose of illustration, system 100 employs, in certain embodiments, a sensor platform 101 that provides collective analysis for sensor data as well as for application data use, where analysis of application data use is enhanced. To do so, system 100 may provide a publisher-subscriber-like architecture allowing for communication between various sensor devices and sensor agents associated with sensor devices. As an extension, the "chat room"-type architecture of system 100 may be part of a tiered implementation, where analysis that takes place as a function of communication in the pub-sub-like forum is amplified as part of a shared community via vertical integration. In one embodiment, sensor platform 101 may be implemented as part of a cloud service. Sensor platform 101 may also, in some embodiments, provide data conversion into one or more universal formats compatible with applications. Such capability in the sensor platform 101 supports vertical integration from sensor devices 103a-103n (or sensor devices 103) to the sensor platform 101, to applications (and therefore businesses or service providers) 105a-105n (or applications 105).

In certain embodiments, vertical integration is functionally combining different components at various levels or forms of data acquisition under a centralized ecosystem created by sensor platform 101. Vertical integration provides seamless interaction between otherwise incompatible units. In one embodiment, vertical integration in system 100 involves the sensor platform 101 building unique capability to integrate sensor device 103a with applications 105 via universal data formatting and device discovery. In other words, sensor devices 103 are endpoints with embedded intelligence allowing the sensor device 103a to provide data to the sensor platform 101; the sensor platform 101, in turn, contains intelligence specific to permitting applications 105 to use data from the sensor platform 101. Sensor platform 101 is thus a central service relative to a collection of sensor devices 103 that provides the means of building communications intelligence between sensor device 103a, or direct sensors, and applications 105, all existing within a particular ecosystem. In one embodiment, the intelligence includes converting data into universal formats, for example, converting data obtained from sensor device 103a into a universal format, then interfacing with applications 105 that use data in the universal format.

In one embodiment, gateway 107 transmits sensor data to the sensor platform 101 for the sensor platform 101 to convert into a universal data format. For gateway 107 to provide an interface between sensor devices 103 and the sensor platform 101, the sensor platform 101 may provide a gateway 107 with compatibility software to vertically integrate detected sensor devices 103 with the sensor platform 101. In one embodiment, gateway 107 may provide consistency or uniformity in the process of transmitting sensor data to the sensor platform 101. For example, gateway 107 may assign identifiers to collected sensor data, providing a means recognition of the data understandable by the sensor platform 101, independent of users or the sensor devices 103. The gateway 107 may also provide authentication or encryption means for collected data so that the sensor platform 101 may use and analyze the data without compromising user security.

As used herein, a "sensor device" refers to a separate physical device that interfaces with a computing device 123 (as in sensor device 103a) or a single hardware that has the functionality of a sensor and a computer (e.g., a smart phone with a sensor application). It is noted that each of the sensor devices 103 may utilize a computing device 123 (e.g., mobile phone, laptop, or netbook, etc.) to communicate over a personal area network (PAN) 109 (or a local area network). In one embodiment, gateway 107 may be deployed as a customer premise device (e.g., a user gateway) to detect announcement signals from the sensor device 103a, where the gateway 107 automatically begins collecting data from the sensor device 103a. For example, the gateway may communicate with the sensor device 103a and/or a computing device 123 associated with the sensor devices 103a via a PAN 109, whereby the gateway 107 may continually scan the PAN 109 for sensor announcement signals.

Upon detecting sensor devices 103, the gateway 107 may prompt sensor devices 103, including itself, to install software that vertically integrates the newly detected sensor devices 103 with sensor platform 101. In this way, sensor platform 101 may automatically receive data from the sensor devices 103 without prompting active user registration. The vertical integration between the sensor platform 101, gateway 107, and sensor device 103a may include end-to-end architecture functions to construct one or more building communication interfaces between these three components to allow data flow from sensor device 103 to the sensor platform 101.

According to one embodiment, after at least one sensor device 103a is automatically registered to a user and gateway 107, the policy engine 111 may facilitate communication among the various sensor devices 103 within the gateway 107. The policy engine 111 that may enhance data processing and control before the data reaches the sensor platform 101 or other actuators by facilitating coordinated communication among the various sensor devices 103 within the gateway 107. For example, the gateway 107 may be a user's mobile phone, while the sensor device 103a may be a glucose meter and the sensor device 103b may be a health bracelet. The policy engine 111 may then determine that the sensor device 103a may communicate with sensor device 103b and incorporate the glucose meter readings into health bracelet exercise trackers. In addition the policy engine may be configured on the fly to associate a short circuit control path to a nearby actuator or sensor. Nearby in this context refers to components that may have a relatively short communication path whose performance metrics are known by the policy engine and are selected by same to improve performance of the overall system. The gateway 107 may then transmit the resulting, processed data to the sensor platform 101 so that data in the sensor platform 101 is more readily usable by applications 105. According to one embodiment, the gateway 107 and policy engine 111 may adapt to future device formats such that these systems may be compatible with future sensor devices and their data formats.

In certain embodiments, gateway 107 may automatically register sensor devices 103 to the sensor platform 101. In one embodiment, the sensor platform 101 may prompt the gateway 107 to register or scan only for certain types of data capable of being converted to a universal data type. For example, a sensor platform 101 interfacing with healthcare-related applications may configure gateway 107 to scan only for sensor devices 103a-103b collecting Food and Drug Administration (FDA)-compliant data. Once the devices are registered with the sensor platform 101, the sensor platform 101 may coordinate, for example, a publisher-subscriber chat room-style communication among the various sensor device 103. There may exist a rendezvous point in this communication forum that is controlled by the policy engine through an access control list. This list may be configured, changed or tuned over the course of the data communication session or running time to provide enhanced security or other performance improvements.

By extension of the registration, gateway 107 may be designated as pertaining to a user and/or location. For example, the sensor platform 101 may recognize gateway 107 as "User 1's gateway" or as "Home." In one embodiment, the sensor platform 101 may include saving collected sensor data in a federated system that permits data from various sensor devices 103 to be accessed according to user or user device identification. The gateway 107 may receive and organize sensor data such that new sensors or sensor data feeds are pluggable, thereby preparing any new data detected within a given PAN 109 for processing in the sensor platform 101 regardless of sensor or data type. In other words, the gateway 107 may operate in a scalable, bus-type model that forms the interface between raw sensor data feeds and the sensor platform 101.

Additionally, the sensor platform 101 may map services and devices to a particular user so that collected sensor data is associated with at least one user. In this way, the sensor platform 101 may serve as a centralized service that retrieves and accesses user and device information, regardless of the user's location. Then, user services and/or applications may centrally access the data at the sensor platform 101 (provided that the sensor platform 101 verifies that the services and/or applications are authorized to access the user and/or device information). The sensor platform may carry information on behalf of other sensors assigned to other users through a sharing arrangement that may be preconfigured or configured at run time. When forwarding information or when sending PAN information the sensor platform may need to digitally sign the data payload or portions of it to ensure a chain of evidence and provide traceability and authenticity for applications in certain markets. The sensor platform may be required to collect and report these signatures from time to time by the centralized server or other applications within the system.

Sensor platform 101 can also utilize third party sensor data feeds 121, or indirect sensors, which may include data that has been already collected and processed by third parties and/or data not directly associated with one or more users and/or devices; the third party sensor data feeds 121 may be used to supplement or augment the trend analyses. For example, the third party sensor data feeds 121 can relate to environmental condition information (e.g., outdoor temperature, weather data, etc.) or other data that may be relevant.

As previously discussed, the sensor platform 101 may further provide vertical integration with applications 105 so that applications 105 may take advantage of the collective sensor data. In other words, sensor platform 101 may vertically integrate these applications 105 by determining data formats used by the applications 105 and converting collected sensor data to the data formats common among various applications 105. To this end, sensor platform 101 may include a data converter that converts raw sensor data into a universal format compatible with applications. In doing so, applications may tap into the data resources of system 100 without application providers needing to code separately for compatibility.

The popularity of user-related sensor devices 103 (e.g., bracelets that can track exercise and sleep habits or mobile phones that utilize a pedometer application) has created consumer-friendly sensors for a wide range of services. For example, a user wanting to improve his health may acquire a pedometer to monitor the number of steps the user takes. As a sensor device, the pedometer may track the number of steps over a period of time (e.g., week or month), and the collected data is analyzed for upward and downward trends in the user's steps for the given period of time.

Vertical integration enables sensor devices to work in concert as data is fed into the common pool of sensor platform 101, wherein the collective data can be used beyond the particular sensor device's targeted purpose. For example, pedometers can collect activity data, while sleep sensors independently collect data on sleep quality, patterns, and cycles, despite correlations between exercise and sleep. Unaware of the interplay between this data, a user of both devices may not readily set up a common application to monitor the relationship between the data sets outside of a unified system. Vertical integration would enable the seamless interfacing of different sensor devices. For instance, sensor platform 101 may permit pedometer data to be analyzed in conjunction with sensors that track the user's quality of sleep. Additionally, this data may lend insight into marketing and business interests. For example, the data from sensor devices may identify the spending habits of users as to correlate health and fitness habits with product recommendations. Additionally, the system 100 may determine that collected metadata indicates a geographic concentration of particularly active people. The system 100 may then determine the information by analyzing data collected from mobile phone pedometers. Alternately, the system 100 may determine the concentration of active people through analysis of application usage of data, facilitated by providing conversion of data into a common data format. In one instance, fitness and marketing companies may then provide applications and plan marketing targets based on the collected metadata analysis. Various forms of this vertically integrated data may be used as part of the digital signature that is included by default in the metadata and collected as part of the notification process of the users interaction with the use of the data.

In another scenario, the sensor platform 101 may be deployed to improve healthcare professionals' examinations of patients. For instance, sensor devices 103 may constantly monitor the vital signs of a particular user. When the user visits his doctor, the doctor may ask about the user's health habits and form her own recordings of the user's health. Conventionally, the doctor's records are separate from the user's sensor devices' tracking, despite possible overlap between the data sets. Therefore, there is a clear lack of integration of systems and data under the traditional approaches. Alternatively, a healthcare company may subscribe to sensor data and metadata acquired from sensor devices that are registered to their clients in the sensor platform 101. After the sensor platform 101 collects and converts client sensor device data and metadata, applications of the healthcare company may download this data and metadata into their database(s). In certain situations, that authenticity of the data may be used to develop a ranking of the data relative to the trust of the source or the trust of the delivery method. This authenticity allows the end user or end application to determine whether to discount or accredit the value of the data as the data is being received and or used. With this database, the healthcare company may respond to members' various health readings in real time or monitor client health statuses for insurance and payment purposes. When the same user's sensor devices are integrated into sensor platform 101, the user's healthcare professional may have access to the user's sensor data immediately before and during the user's medical examination. This data may provide more accurate recordings than what the user may be able to provide based on his subjective memory or impressions. In addition, the system may perform an automated task that actuates a mechanism such as an audible alarm or mechanical pump for example that is required in order to intervene within a timeframe that is well defined relative to the known responsively of the entire system.

In another healthcare use case, the system 100 may link a blood pressure monitor sensor device 103a to sensor platform 101 so that corresponding healthcare applications may provide a particular service to the user. As such, the sensor platform 101 and/or user gateway 107 may detect blood pressure sensor 103a. It is noted that the blood pressure sensor 103a may be part of a wearable device, according one embodiment. The gateway 107 may extract data measurements from the blood pressure sensor device 103a and transfer the data to the sensor platform 101, whereby healthcare application 105a may deliver the data to the user's healthcare company. According to one embodiment, the user's blood pressure readings are routinely reported to and monitored by the healthcare company by way of application 105a by sensor platform 101. For example, if a user's blood pressure reaches a predetermined unhealthy range, the sensor platform 101 may notify the user as well as a designated user (e.g., user's family member) (based on profile information supplied by sensor platform's profile database) or the user's healthcare company via application 105a.

Furthermore, sensor platform 101 may provide aggregate trend analysis across multiple users. This aggregate trend analysis may be classified according to subject matter. For example, in addition to collecting one user's pedometer data, platform 101 may aggregate pedometer data from multiple pedometers and recognize patterns from the collective data set. In one instance, aggregate pedometer data may indicate that people tend to run in the morning or people tend to bike on the weekends. Furthermore, sensor platform 101 may analyze the pedometer data with respect to location information, e.g., global positioning system (GPS) coordinates. Such analysis may reveal certain patterns that are not detectable by individual data sets, such as Californians run outdoors or urbanites tend to run indoors. In this manner, platform 101 can pool the data in a central repository where data produced for the same subject can be analyzed collectively. Vertically integrating applications in system 100 may also provide the sensor platform with more input to analyze. For example, the system 100 may include application usage of sensor data in its analysis.

Also, users may initiate uploading of sensor data to computing devices and social networking groups, for further analysis or to compare personal measurements against that of other users. For instance, users may subscribe to groups whose members encourage one another to meet fitness goals by comparing data to predetermined threshold values. Therefore, popular usage creates a data intensive environment where users and applications independently create prolific sources of data.

In a further embodiment, the system 100 may elect to run various components of the system in concert, or independently. For example, the system 100 may run one operation simultaneously but independently of another operation, then engage two or more components running the operations to "catch up" with other components to operate the system 100 as a whole. For example, sensor devices 103 may all, independently, collect data. In one embodiment, the system 100 may involve one or more gateways 107 processing or storing the data. Then, at a later time, the gateways 107 may transfer the data to the sensor platform 101, where the data processing within sensor platform 101 then "catches up" with data already processed by the sensor platform 101. In another instance, sensor devices 103 may all independently collect and transfer data to the sensor platform 101. Then, sensor platform 101 may engage yet a new application 105a and determine a new data format. Then, sensor platform 101 may prompt data transfer from the sensor devices 103 and convert data to a format compatible with the new data format of the application 105a. In doing so, the sensor platform 101 responds to new information received within system 100 by causing sensor device data transmission to "catch up" to new application interaction.

For illustrative purposes, the networks 113-119 may be any suitable wireline and/or wireless network, and be managed by one or more service providers. For example, telephony network 115 may include a circuit-switched network, such as the public switched telephone network (PSTN), an integrated services digital network (ISDN), a private branch exchange (PBX), or other like network. Wireless network 113 may employ various technologies including, for example, code division multiple access (CDMA), enhanced data rates for global evolution (EDGE), general packet radio service (GPRS), mobile ad hoc network (MANET), global system for mobile communications (GSM), 4G long-term evolution (LTE), Internet protocol multimedia subsystem (IMS), universal mobile telecommunications system (UMTS), etc., as well as any other suitable wireless medium, e.g., microwave access (WiMAX), wireless fidelity (WiFi), satellite, and the like. Meanwhile, data network 119 may be any local area network (LAN), metropolitan area network (MAN), wide area network (WAN), the Internet, or any other suitable packet-switched network, such as a commercially owned, proprietary packet-switched network, such as a proprietary cable or fiber-optic network.

Although depicted as separate entities, networks 113-119 may be completely or partially contained within one another, or may embody one or more of the aforementioned infrastructures. For instance, the service provider network 117 may embody circuit-switched and/or packet-switched networks that include facilities to provide for transport of circuit-switched and/or packet-based communications. It is further contemplated that networks 113-119 may include components and facilities to provide for signaling and/or bearer communications between the various components or facilities of system 100. In this manner, networks 113-119 may embody or include portions of a signaling system 7 (SS7) network, or other suitable infrastructure to support control and signaling functions. In addition the system may operate as separate parts that rendezvous and synchronize periodically to form a larger system with similar characteristics.

According to exemplary embodiments, end user devices (not shown) may be utilized to communicate over system 100 and may include any customer premise equipment (CPE) capable of sending and/or receiving information over one or more of networks 113-119. For instance, voice terminal may be any suitable plain old telephone service (POTS) device, facsimile machine, etc., whereas mobile device (or terminal) may be any cellular phone, radiophone, satellite phone, smart phone, wireless phone, or any other suitable mobile device, such as a personal digital assistant (PDA), pocket personal computer, tablet, customized hardware, etc. Further, computing device may be any suitable computing device, such as a VoIP phone, skinny client control protocol (SCCP) phone, session initiation protocol (SIP) phone, IP phone, personal computer, softphone, workstation, terminal, server, etc.

System 100 is additionally detailed in co-pending application, entitled, "Machine-To-Machine Sensor Data," which is incorporated herein by reference in its entirety.

Figure 2A:
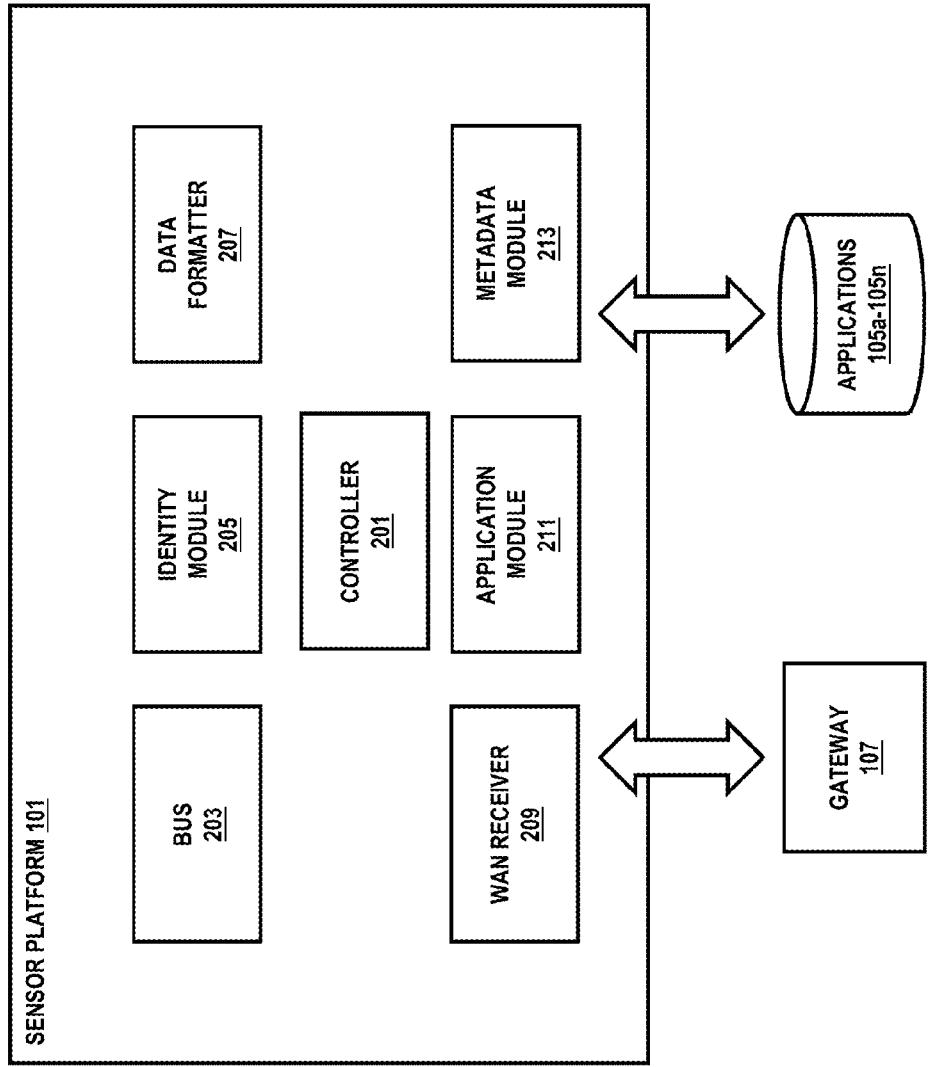
FIG. 2A is a diagram of a sensor platform capable of registering various sensor devices, according to one embodiment.

FIG. 2A is a diagram of a sensor platform capable of registering various sensor devices, according to one embodiment. The sensor platform 101 contains a controller 201, bus 203, identity module 205, data formatter 207, WAN receiver 209, application module 211, and metadata module 213. The sensor platform 101 may communicate with the gateway 107 to receive sensor data and convey the data to applications 105. In one embodiment, the sensor platform 101 may process the data to facilitate use by the applications 105. The gateway 107 may supply the sensor platform 101 with data and metadata from various sensor devices 103.

The controller 201 performs control logic functions and facilitates coordination among the other components of sensor platform 101. In one embodiment, the bus 203 is a communication vehicle that transmits data and metadata among the gateway 107, applications 105, and all the various components within the sensor platform 101. The identity module 205 may register new user device and gateway pairs and store the information of current user device gateway pairs. An example embodiment of the identity module 205 may include an identification system (IS) to provide assurance of associations between users and user devices, as well as security for transmitted sensor data. The identification system is a security application that facilitates strong authentication to web sites, applications, and networks by providing access only after providing a registered identification system identity. According to one embodiment, the identification system registration process may provide further security by requiring an activation code. Registration and authentication may occur several times over the course of the data identification system events without the applications being disrupted from their normal operation. This authentication may be controlled by a proxy mechanism which is part of the sensor platform.

The data formatter 207 may receive data in various formats and convert this data into a universal format usable in applications 105. The data formatter 207 may have a different connector for different types of data streams. According to one embodiment, the data formatter 207 may include one connector dedicated to a sensor data stream and another connector dedicated to a video data stream. Each of these connectors may feed into a respective formatter depending on the original data format. Once the data formatter 207 converts the data feeds into a universal format, a stream controller may usher the converted data and metadata into a connector that feeds the newly formatted data onto the bus 203. Bus 203 may then distribute converted data to the applications 105.

The WAN receiver 209 may contain both direct and indirect receiver components that accept data from both direct and indirect sensor devices though the bus 203. The application module 211 may manage the various applications which downloads and monitors the data from the sensor platform 101, tracking applications that fall to misuse and allotting system resources based on application activity. The metadata module 213 may store and manage trend metadata that attached to the data sent from the various sensor devices 103 and third party sensor data feeds 121.

Figure 2B:
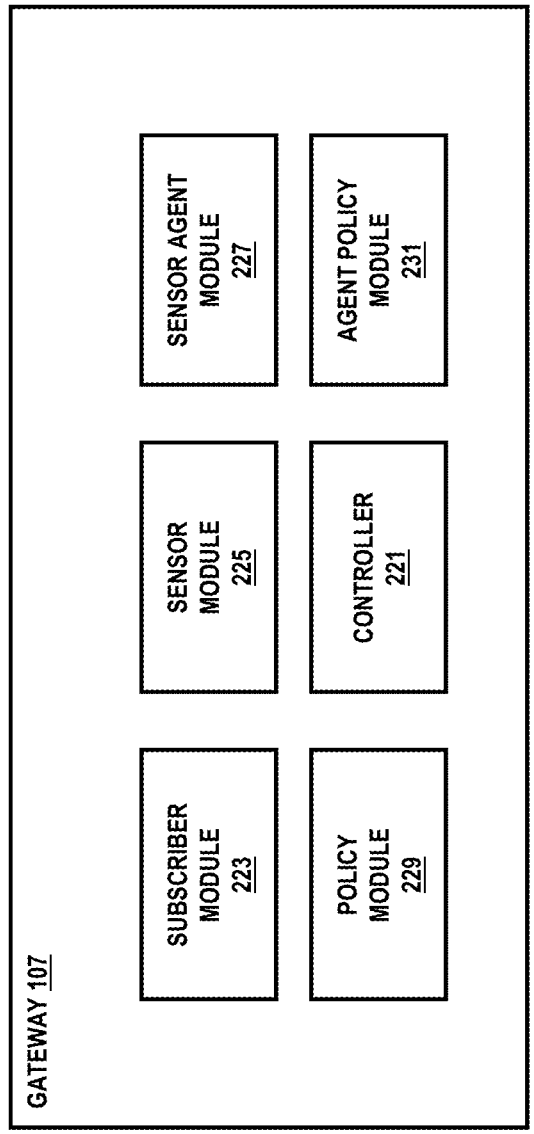
FIG. 2B is a diagram of a gateway device capable of extracting sensor data and delivering the data to a sensor platform, according to one embodiment.

FIG. 2B is a diagram of a gateway device capable of extracting sensor data and delivering the data to a sensor platform. Gateway 107 may comprise of computing hardware (such as described with respect to FIG. 14), as well as include one or more components configured to execute the processes described herein for providing the sensor to cloud processing services of system 100. In one implementation, gateway 107 includes controller 221, subscriber module 223, sensor module 225, sensor agent module 227, policy module 229, and agent policy module 231. Gateway 107 may also communicate with the WAN and PAN 109. While specific reference will be made to this particular implementation, it is also contemplated that gateway 107 may embody many forms and include multiple and/or alternative components. For example, it is contemplated that the components of gateway 107 may be combined, located in separate structures, or separate locations.

The controller 221 and subscriber module 223 may be configured to determine the presence of one or more senor devices in the PAN 109 network. The sensor module 225 and controller 221 may associate sensor devices 103 found by subscriber module 223 and controller 221 in the PAN 109 with one or more user accounts. Once a sensor device 103a is associated with a user account, controller 221 may communicate the association communicate to sensor platform 101 when the data is transmitted by way of networks 113-119, PAN 109, or WAN. It is contemplated that a single user account may be associated with multiple sensor devices within a single gateway 107. According to one embodiment, the sensor data may be saved in the sensor platform's federated system according to the user account associations assigned to the data by the subscriber module 223 and controller 221. Sensor agent module 227 and controller 221 may log and track the various sensor agents in the PAN 109 network, as well as monitor these sensor agents' activity level, or lack thereof. According to one embodiment the subscriber module 223 and the controller 221 may create new sensor agents in one or more gateway devices thus providing redundant, federated data collection systems. According to another embodiment, the sensor agent module 227 may perform data conversion. For example, the sensor agent module 227 may convert the units for a thermostat from Fahrenheit to Celsius.

The policy module 229 may determine the various data communication levels among the sensor agents in one or more gateway devices. The policy module 229 may also determine the data communication that the sensor agents may engage in with the sensor platform through the networks 113-119, WAN, and PAN 109. The agent policy module 231 and the controller 221 may facilitate organized and coordinated communication among the various PAN 109 sensor agents in the gateway device and the sensor platform and between gateway devices that are used to dynamically manage PAN networks over the course of the data collection event. This communication may allow each PAN 109 sensor agent autonomous communication flexibility within the gateway device with other PAN 109 gateway devices and the sensor platform. The agent policy module 231 may be a medium of communication among the various PAN 109 sensor agents as dictated by policy module 229 and controller 221.

Figure 2C:
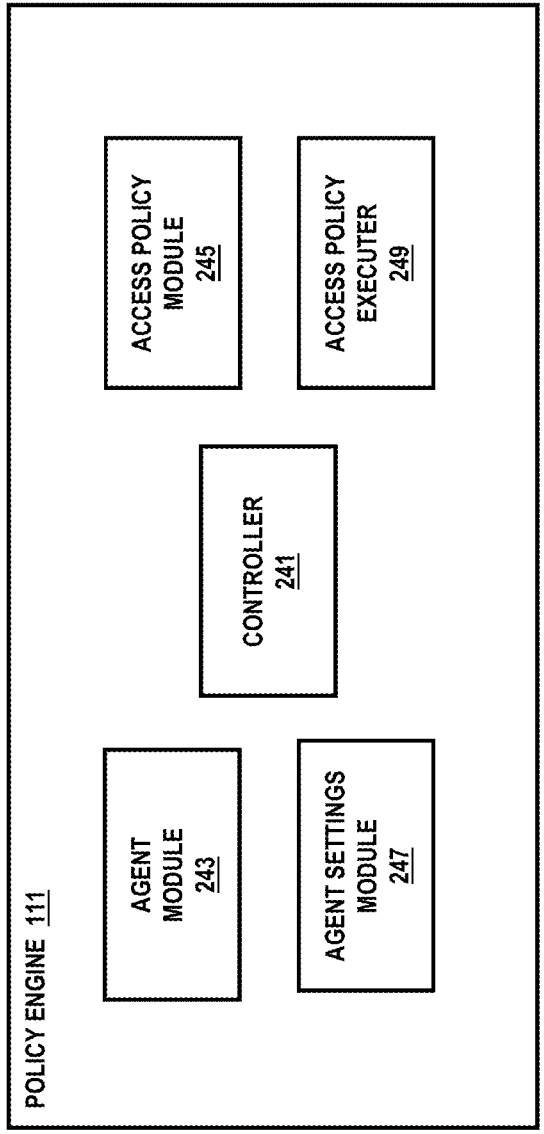
FIG. 2C is a diagram of a policy engine capable of controlling communications among the sensor agents, according to one embodiment.

FIG. 2C is a diagram of a policy engine capable of controlling communications among the sensor agents, according to one embodiment. Policy engine 111 may comprise computing hardware (such as described with respect to FIG. 14), as well as include one or more components (e.g., software, firmware, specialized hardware, or a combination thereof) configured to execute the processes described herein for providing the sensor to cloud processing services of system 100. In one implementation, policy engine 111 includes controller 241, agent module 243, access policy module 245, agent settings module 247, and access policy executer 249. Policy engine 111 may also communicate over a WAN, which may be formed by any combination of the networks 113-119. User devices and sensor devices 103 associated with user devices may access policy engine 111 via the gateway 107. While specific reference will be made to this particular implementation, it is also contemplated that policy engine 111 may embody many forms and include multiple and/or alternative components. For example, it is contemplated that the components of policy engine 111 may be combined, located in separate structures, or separate locations.

In one embodiment, the controller 241 and agent module 243 may be configured to determine the presence of one or more agents, including sensor agents. For example, the gateway 107 may include an agent application programming interface (API) that communicates with all the agents associated with a gateway 107. The controller 241 and agent module 243 may then interact with the API to determine the agents associated with a gateway 107. The access policy module 245 may contain the access policy. For example, access policy include an access control list (e.g., in template form) dictating possible communication access controls among sensor agents. For instance, the access policy may include a set of settings relating to access rights. The controller 241 and access policy module 245 may then maintain and update the access policy for access by other modules of the policy engine 111.

Then, the controller 241 and agent settings module 247 may determine each agent's control settings with respect to the access policy. For example, the agent policy may permit sensor agents to select access to other sensor agents that process, for example, sensor data relating to temperature. The controller 241 and agent settings module 247 may determine whether a given sensor agent, for example, sensor agent A, requests access to other agents that process temperature sensor data, or if other sensor agents that process temperature sensor data may communicate with sensor agent A. The controller 241 and access policy executer 249 may then translate the settings into a format that can be applied to the access policy module 245. For example, if the agent settings module 247 dictates that sensor agent A may communicate with all sensor agents that process temperature sensor data, the access policy executer 249 may determine that sensor agents B, C, and F process temperature sensor data and translate the settings such that sensor agent A may communicate with sensor agents B, C, and F. By extension, the access policy module 245 may set up a "chat room" interface for the sensor agents A, B, C, and F to communicate.

Figure 2D:
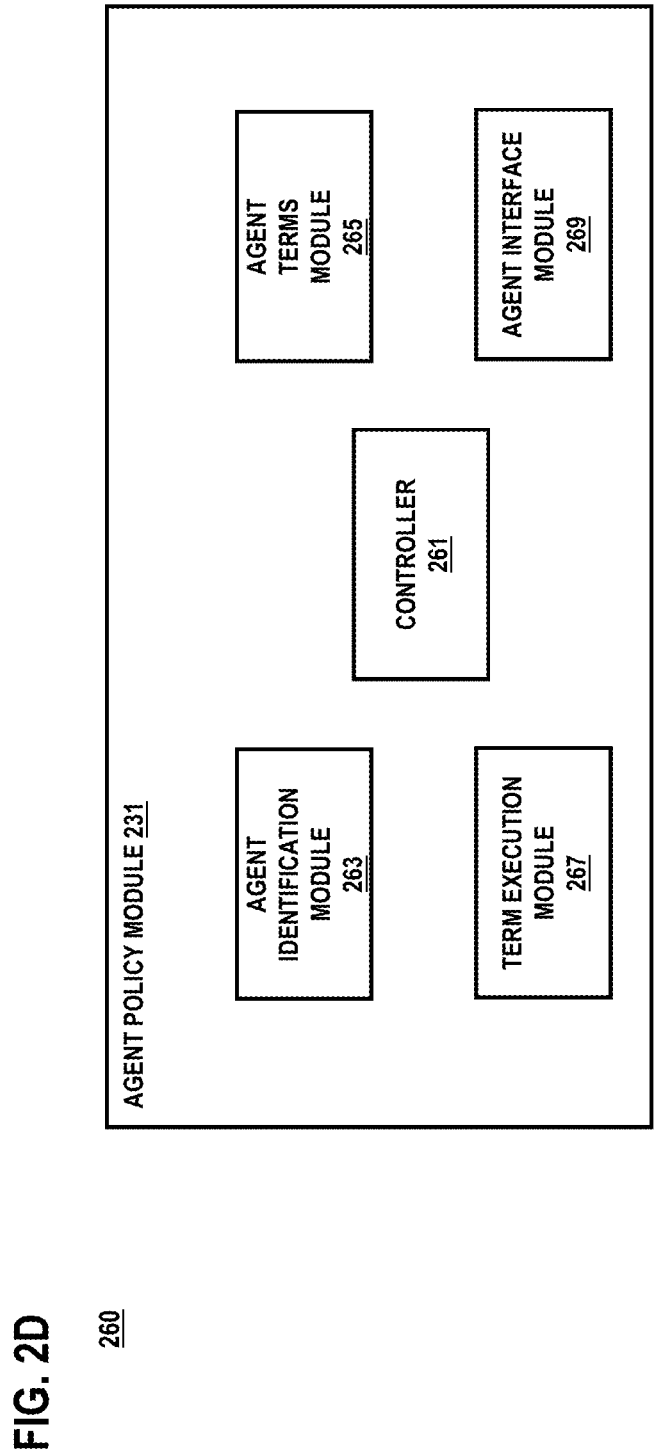
FIG. 2D is a diagram of an agent policy module utilized in the policy engine of FIG. 1, according to one embodiment.

FIG. 2D is a diagram of an agent policy module utilized in the policy engine of FIG. 1, according to one embodiment. Agent policy module 231 may comprise computing hardware (such as described with respect to FIG. 14), as well as include one or more components (e.g., software, firmware, specialized hardware, or a combination thereof) configured to execute the processes described herein for providing the sensor to cloud processing services of system 100. In one implementation, agent policy module 231 includes controller 261, agent identification module 263, agent terms module 265, term execution module 267, and agent interface module 269. User devices and sensor devices 103 associated with user devices may access the agent policy module 231 via the gateway 107 or directly via a WAN. While specific reference will be made to this particular implementation, it is also contemplated that agent policy module 231 may embody many forms and include multiple and/or alternative components. For example, it is contemplated that the components of the agent policy module 231 may be combined, located in separate structures, or separate locations.

In one embodiment, the agent policy module 231 may include an agent identification module 263 that identifies an agent to the policy engine 111. For example, the controller 261 may and agent identification module 263 may register a unique identifier associated with an agent. Alternately or in addition, the controller 261 and agent identification module 263 may identify agents according to sensors, devices, users, and/or sensor data associated with a given agent. Then, the controller 261 and agent terms module 265 may extract agent access control setting terms from the policy engine 111. For example, the controller 261 and agent terms module 265 may determine that a given agent A has setting terms that permit agent A to communicate with agent B.

The controller 261 and agent terms module 265 may further comprise of a means of tracking and recording the creation and removal of the terms. For instance, the controller 261 and agent terms module 265 may continually determine new terms or determine outdated terms. Then, the controller 261 and agent terms module 265 may revise agent terms to reflect current terms or suggest new terms for use. Furthermore, the controller 261 and agent terms module 265 may track and record usage and popularity of the setting terms, past, present, and future.

The controller 261 and term execution module 267 may then determine relevant terms for communication. For example, the controller 261 and term execution module 267 may contact both agent A and agent B to initiate interaction. In addition, the controller 261 and term execution module 267 may determine limitations within the setting terms. For instance, agent A's access terms may dictate that agent A permits communication with agent B for only a subset of data associated with agent A. The controller 261 and term execution module 267 may recognize this limitation and translate the term for the controller 261 and agent interface module 269 when the controller 261 and agent interface module 269 set up a communication forum in accordance with the terms. These terms may also be discovered locally based on the reputation of the various components in the system.

Figure 3A:
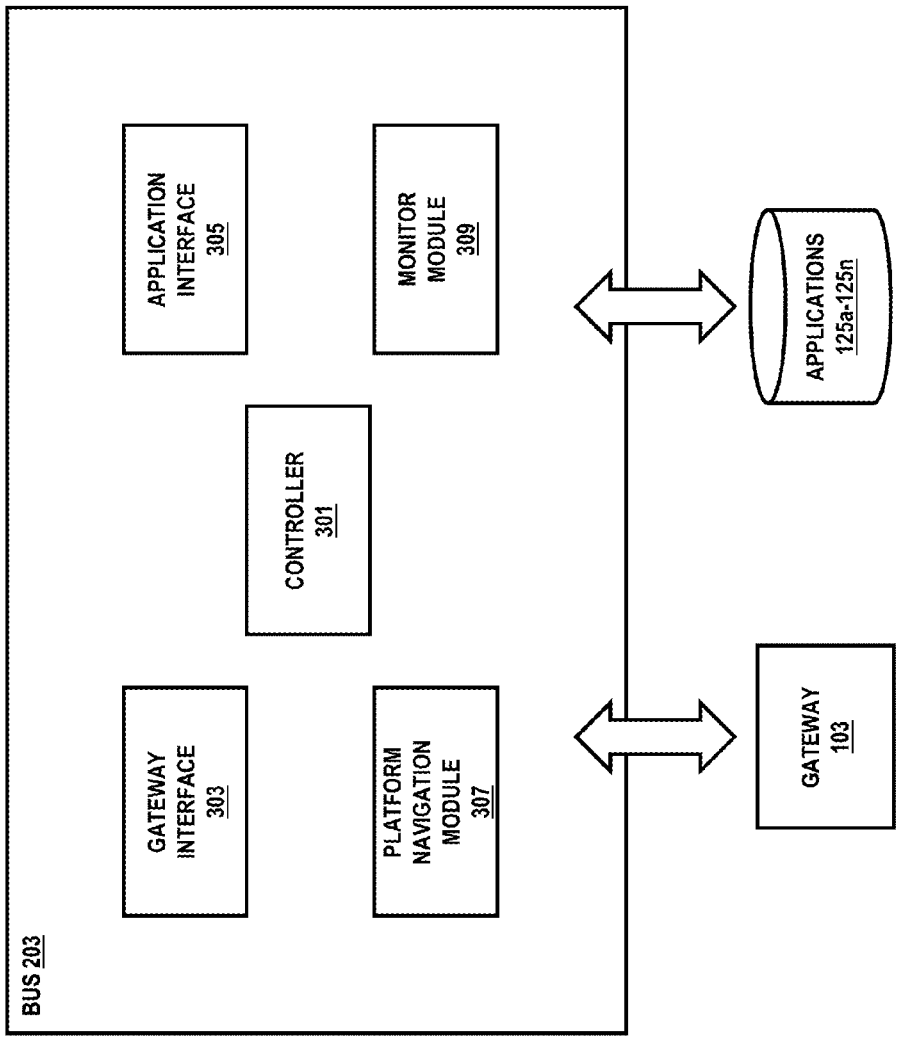
FIG. 3A is a diagram of a bus architecture used in the sensor platform of FIG. 1, according to one embodiment.

FIG. 3A is a diagram of a bus-type architecture used in the sensor platform of FIG. 1, according to one embodiment. The bus-type architecture may be represented with bus 203. Bus 203 may comprise computing hardware (such as described with respect to FIG. 14), as well as include one or more components configured to execute the processes described herein for providing the sensor to platform processing services of system 100. In one implementation, bus 203 includes controller 301, gateway interface 303, application interface 305, platform navigation module 307, and monitor module 309. Bus 203 may also communicate with the wide area network (WAN). User devices and sensor device 103 associated with user devices may access the bus 203 via the PAN 109. While specific reference will be made to this particular implementation, it is also contemplated that bus 203 may embody many forms and include multiple and/or alternative components. For example, it is contemplated that the components of the bus 203 may be combined, located in separate structures, or separate locations.

In one embodiment for execution of system 100, the controller 301 of bus 203 may receive, through the gateway interface 303, data output from the agents. For example, the controller 301 and gateway interface 303 may interact with gateway 107 through the PAN 109 to receive the data output. The bus controller 301 may also receive, through the application interface 305, requests for data from the applications 105. The controller 301 may then prompt platform navigation module 307 to match data stored to the data requests. For example, the controller 301 and platform navigation module 307 may navigate the sensor platform 101 to locate data stored in the sensor platform 101. As previously discussed, data stored in the sensor platform 101 may initially enter the sensor platform 101 via the PAN 109 and controller 301 and gateway interface 303 of bus 203. The monitor module 309 may monitor the WAN for more applications or gateways and add communication channels for the applications and gateways to the platform. For example, the controller 301, gateway interface 303, application interface 305, and monitor module 309 may interact such that the monitor module 309 prompts additions to the gateway interface 303 and/or application interface 305 as it detects new applications and gateways.

Figure 3B:
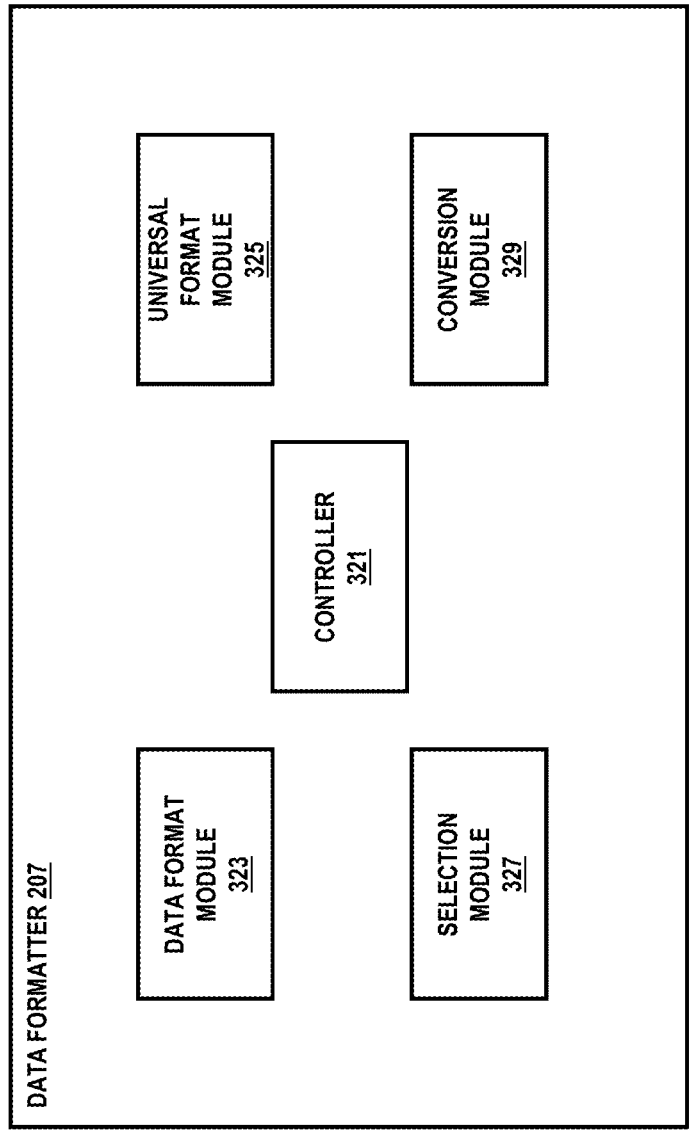
FIG. 3B is a diagram of a data formatter capable of converting raw sensor data into a common format, according to one embodiment.

FIG. 3B is a diagram of a data formatter capable of converting raw sensor data into a common format, according to one embodiment. Data formatter 207 may comprise computing hardware (such as described with respect to FIG. 14), as well as include one or more components configured to execute the processes described herein for providing the sensor to platform processing services of system 100. In one implementation, data formatter 207 includes controller 321, data format module 323, universal format module 325, selection module 327, and conversion module 329. Data formatter 207 may also communicate with the wide area network (WAN). User devices and sensor device 103 associated with user devices may access the bus 203 via the PAN 109 and WAN. While specific reference will be made to this particular implementation, it is also contemplated that data formatter 207 may embody many forms and include multiple and/or alternative components. For example, it is contemplated that the components of the data formatter 207 may be combined, located in separate structures, or separate locations.

In one embodiment, the controller 321 and the data format module 323 may determine the data format of received raw sensor data. The universal format module 325 may contain a collection of universal formats. In one embodiment, the system 100 may include several universal data formats formulated for various types of files. For example, text data and media data may include a number of different types of files for each type of input. The universal data format may be universal within the realm of media input. The controller 321 and selection module 327 may then determine a universal format that corresponds to the raw sensor data. Then, the controller 321 and conversion module 329 may convert the raw sensor data into the universal format determined by the selection module 327.

Figure 3C:
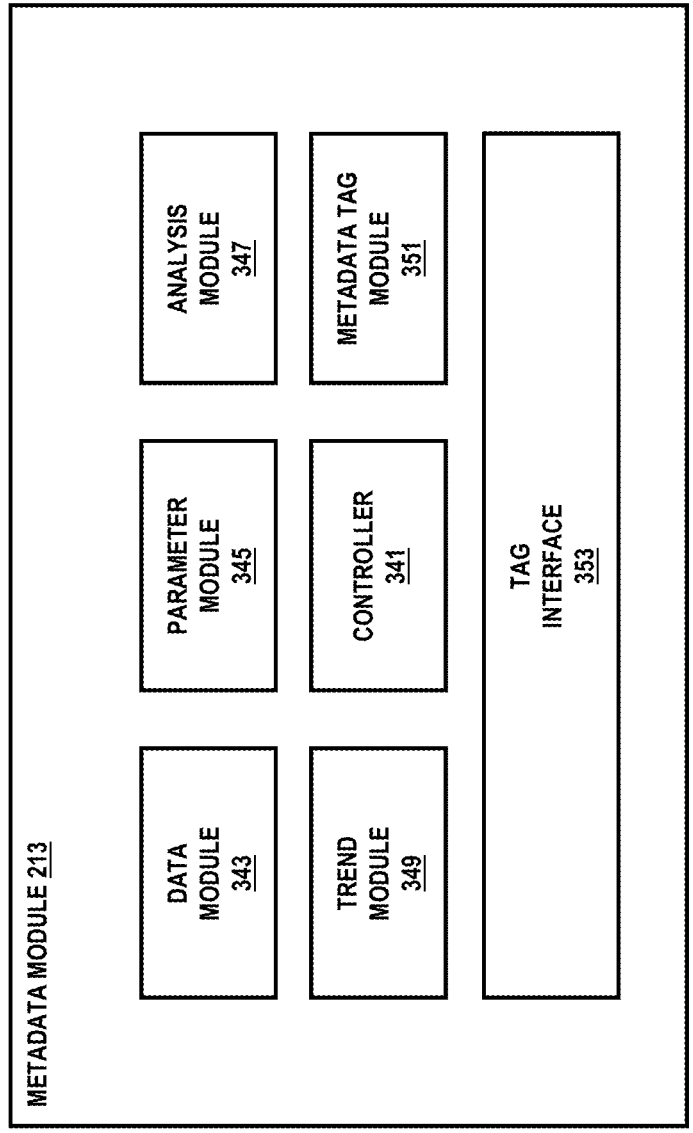
FIG. 3C is a diagram of a metadata module capable of detecting trends and tagging using metadata related to the trends, according to one embodiment.

FIG. 3C is a diagram of a metadata module capable of detecting trends and tagging using metadata related to the trends, according to one embodiment. Metadata module 213 may comprise computing hardware (such as described with respect to FIG. 14), as well as include one or more components configured to execute the processes described herein for providing the sensor to platform processing services of system 100. In one implementation, metadata module 213 includes controller 341, data module 343, parameter module 345, analysis module 347, trend module 349, metadata tag module 351, and tag interface. Metadata module 213 may also communicate with the wide area network (WAN). User devices and sensor devices 103 associated with user devices may access the metadata module 213 via the PAN 109 and WAN. While specific reference will be made to this particular implementation, it is also contemplated that metadata module 213 may embody many forms and include multiple and/or alternative components. For example, it is contemplated that the components of the metadata module 213 may be combined, located in separate structures, or separate locations.

The controller 341 and data module 343 may include the raw sensor data, sensor data as output by agents, and/or data stored in the sensor platform 101. The controller 341 and parameter module 345 may determine one or more parameters to observe regarding the data. For example, parameters for data from a glucose meter may include glucose level. Sensor data may also include parameters such as time of day or ambient temperature. In one embodiment, the controller 341 and parameter module 345 may determine the one or more parameters based on parameters used by applications 105. For instance, where application 105a is an application that helps users reach their fitness goals by offering a support network of users with similar fitness goals. Parameters selected by parameter module 345 may include glucose levels of one user relative glucose levels of a group of users associated with the one user. In providing the service of application 105a, controller 341 may offer application 105a data regarding the success of the application. In another embodiment, the controller 341 and parameter module 345 may determine relationships or correlation between various threads of data and create parameters based on the relationships. For example, by collecting data from various sources, the controller 341 and parameter module 345 may detect glucose levels rising at the same time that ambient temperatures rise. The controller 341 and parameter module 345 may then target glucose level and ambient temperature as parameters.

The controller 341 and analysis module 347 may analyze data based on parameters. In one embodiment, the controller 341 and analysis module 347 may conduct the analysis drawing from all the relevant data stored in the sensor platform 101 or accessible by the sensor platform 101. Based on the analysis, the controller 341 and trend module 349 may then determine if the data falls into any trend or pattern relating to the parameters, or if various collections of data bear any relationship to one another. If the controller 341 and trend module 349 find a pattern or relationship, the metadata tag module 351 may create or identify a metadata tag for the data, relating to the trend or relationship. The tag interface 353 may then tag the data with the metadata tag.

Figure 4:
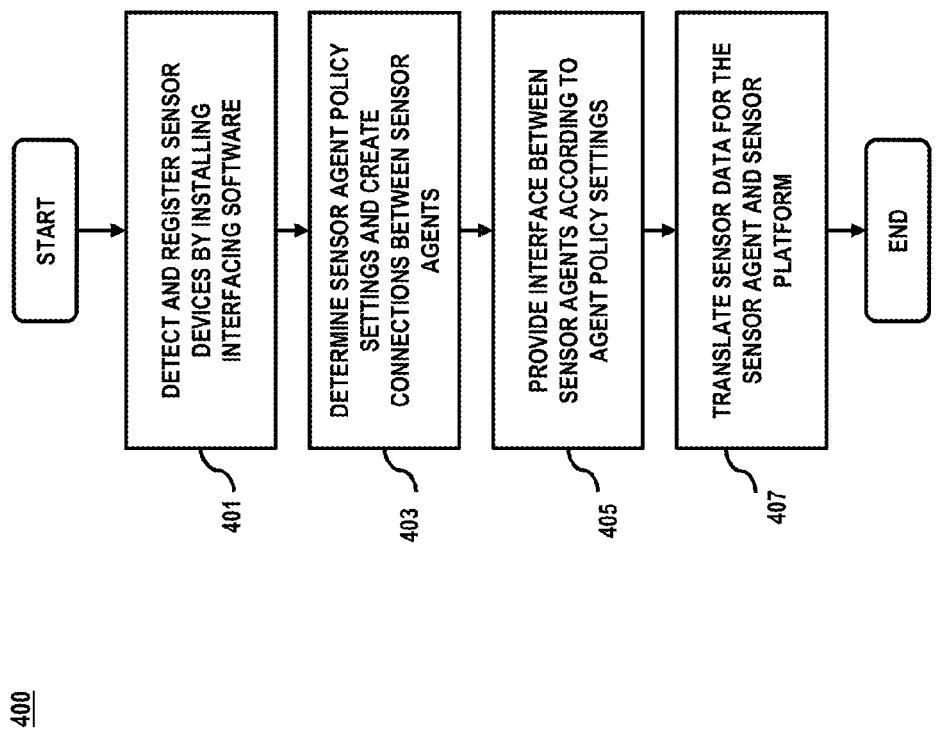
FIG. 4 is a flowchart of a process for discovering, registering, and managing several sensor devices within a gateway device registered to a sensor platform, according to one embodiment.

FIG. 4 is a flowchart of a process for discovering, registering, and managing several sensor devices within a gateway device registered to a sensor platform, according to one embodiment. In one embodiment, this process can be executed by gateway 107 using controller 221. As shown, the process, per step 401, may automatically detect a direct sensors, selectively register the direct sensors, and install an interfacing software into the direct sensors. Next, in step 401, the controller 221 may collect the data in various formats from the sensor devices 103 (which may include direct sensors and/or indirect sensors). In step 403, the controller 221 may receive, from the sensor agents, respective access settings associated with the agents. In step 405, the process can create an interface for communication among the agents based on the access settings. In one embodiment, each device registered to the gateway 107 in the PAN 109 has one or more corresponding sensor agents within the gateway 107. These sensor agents may act autonomously within the gateway 107. Each sensor agent, in certain embodiments, may communicate with other senor agents by publishing to or subscribing from any of the other sensor agents within a chat room-style bus-model. The policy engine 111 within the gateway 107 can thus manage these publications and subscriptions for these sensor agents. In one embodiment, the sensor platform 101 may determine subscriber registration information associated with published data feeds. Also gateways may maintain a record of historical changes such that the change trends can be discovered locally to assist with data collection management and rendezvous opportunities.

According to one embodiment, the interface may be a "chat room" or instant messaging session between agents in accordance with agent control access settings. In this "chat room," the controller 221 may determine one or more characteristics of the data and/or the agents. One or more access rules may be determined based on the characteristics relating to the communication among the agents; the policy engine 111 may be programmed or configured accordingly. In step 407, the sensor data may translate sensor data for the corresponding sensor agent(s) as well as the sensor platform 101. That is, because of the variety of different sensor devices 103, data format conversion is performed to permit communication among the sensor agents and to enable the sensor platform 101 to forward the converted data to a multitude of applications with different data requirements.

Figure 5:
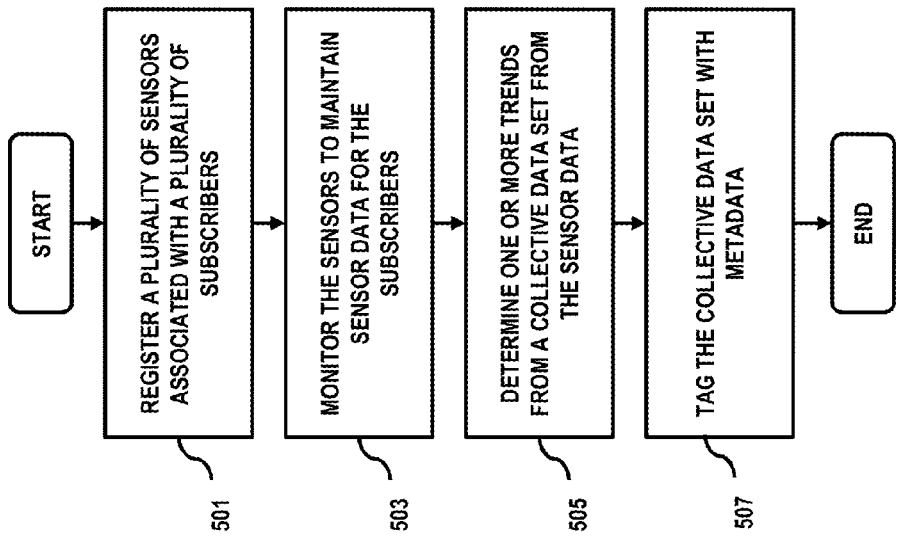
FIG. 5 is a flowchart of a process for determining trends from collected sensor data, according to one embodiment.

FIG. 5 is a flowchart of a process for determining trends in sensor data described above, which may be carried out by an embodiment illustrated in FIG. 2A. In step 501, the controller 201 may dynamically register a plurality of sensors associated with a plurality of subscribers. In one embodiment, the subscribers may include users, devices, gateways, services, or a combination thereof. These subscribers may be direct or indirect. Direct subscribers may include sensors associated with users and/or devices while indirect subscribers may include third parties associated with data feeds. The controller 201 may detect as subscribers, individual sensors, sensors via gateways associated with locations and/or users, service providers, or a combination thereof. Then, the controller 201 may monitor the sensors as part of a sensor platform to maintain sensor data for the plurality of subscribers (step 503). For example, the controller 201 may notice prolonged inactivity of a registered sensor device and remove it from the collection of sensor devices. From the monitoring, the controller 201 may acquire the sensor data from the plurality of sensors as a collective data set to determine one or more trends and tag the collective data set with metadata for the determined trends (steps 505 and 507).

Figure 6:
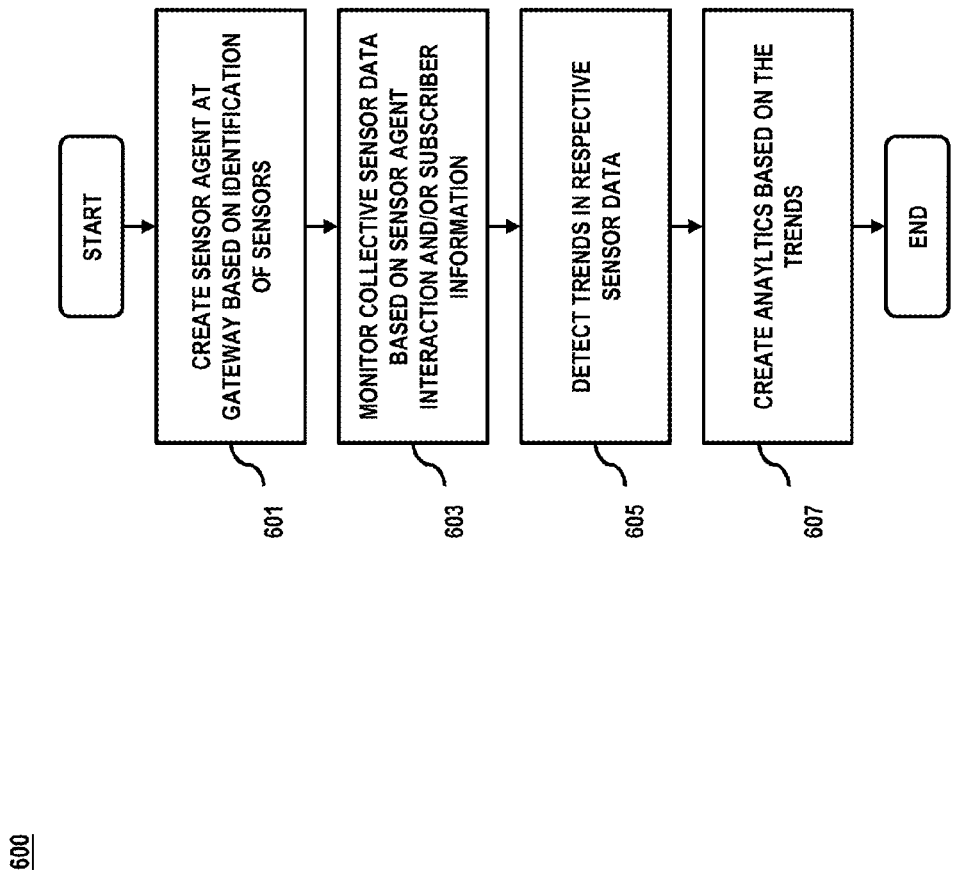
FIG. 6 is a flowchart of a process for developing analytics to determine or verify trends, according to one embodiment.

FIG. 6 is a flowchart of a process for developing analytics to determine or verify trends, according to one embodiment. The process may be carried out by an embodiment illustrated in FIG. 2A. In one embodiment, the controller 201 may further create applications, sensor agents, or a combination thereof based, at least in part, on the metadata. For example, the controller 201 may create a sensor agent at a gateway based on the identification of sensors (step 601). The controller 201 may determine the presence of sensors and cause the sensors to register at gateways that then transfer sensor data to the sensor platform 101. In one scenario, the sensor data is processed by one or more sensor agents prior to reaching the sensor platform. In a further scenario, the gateways may be configured such that sensor agents may communicate with each other. In one case, the communication between sensor agents may further data analysis performed by the sensor platform 101 or prepare sensor data for compatibility with the sensor platform 101. For step 603, the controller 201 may then monitor collective sensor data in relation to sensor agent interaction and/or subscriber information.

For step 605, the controller 201 may detect trends in the sensor data while taking into account processing or communication between sensor agents and subscriber information, for example, user profile information. Upon detecting possible trends, the controller 201 may create analytics based on the trends or analytics to verify the trends for step 607. To take a previous example, the glucose meter and pedometer may be registered at one gateway, each with a corresponding sensor agent. The glucose meter sensor agent and pedometer sensor agent may be in communication such that controller 201 detects an inverse relationship for the data and creates an analytic to verify the trend.

Figure 7:
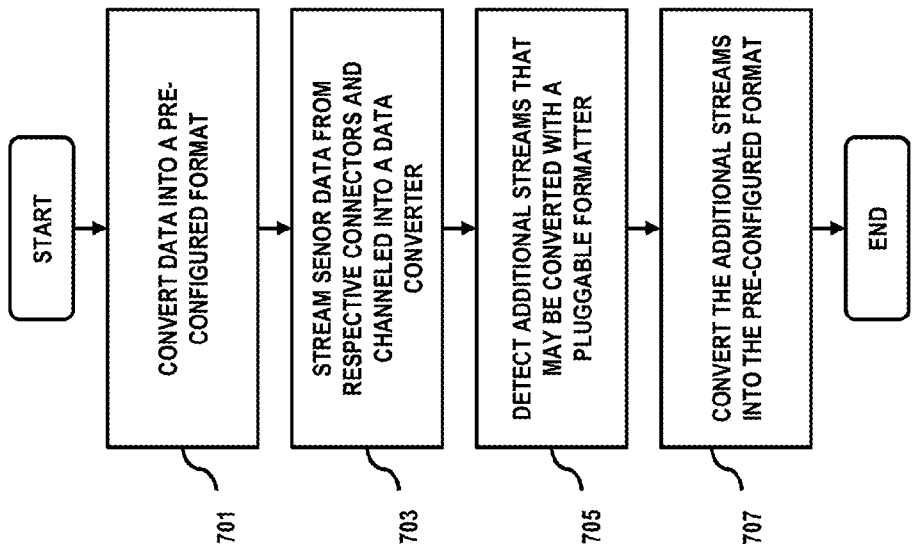
FIG. 7 is a flowchart of a process for extending compatibility for newly discovered sensor data feeds, according to one embodiment.

FIG. 7 is a flowchart of a process for extending compatibility for newly discovered sensor data feeds which may be carried out by an embodiment illustrated in FIG. 2A, for example, by changing the data formats of raw sensor data. Step 701 may include the controller 201 converting the sensor data into a universal data format and delivering the converted data to one or more applications. Possible applications may include healthcare databases or security systems. In one embodiment, the controller 201 may perform the conversion by detecting a data format associated with the sensor data. For example, the controller 201 may stream sensor data into a data converter and further detect any relevant or new sensor feeds to transmit to a data converter (steps 703 and step 705). In one embodiment, the data converter may convert the data into a preconfigured format (step 707). In an additional embodiment, the controller 201 may also create the universal data format based on the detected data format. For example, raw sensor data may be video data. The controller 201 may determine that the data is in a video data format and convert the sensor data into a known, widely compatible data format, or create a data format for the video data that is widely compatible among the applications associated with system 100. For example, controller 201 may make video data taken at a supermarket parking lot available for the supermarket to determine customer flow, but the controller 201 may also parse the video data to render information such as license plates numbers to aid security interests. Controller 201 may convert the video data so that both applications determining customer flow and applications using license plates may make use of it.

Figure 8:
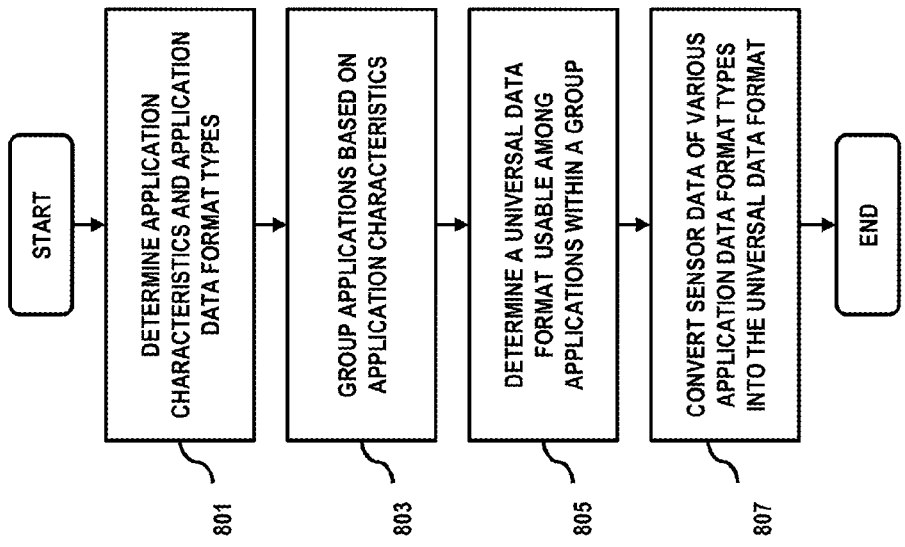
FIG. 8 is a flowchart of a universal data format creation process, according to one embodiment.

FIG. 8 is a flowchart of a universal data format creation process described above which may be carried out by an embodiment illustrated in FIG. 2A, for example, to extend application usage of data that does not already have a known widely-compatible data format. For step 801, the controller 201 may determine one or more characteristics associated with the applications within the system 100. For example, characteristics may include file types transferred by applications 105, functions of the applications, or launch dates of applications. File types may include data types; functions of the applications may include whether the applications are used to give notifications, share data, create user interfaces, etc.; launch dates of applications may include when the application was available for use. Information regarding launch dates may inform data standards suitable for the application. Then, the controller 201 may group the applications based on the characteristics (step 803). For example, the controller 201 may determine that applications 105 use video data and create a group where all the applications use video data.

The controller 201 may create the universal data format based on the application grouping (step 805) and convert data to the created universal data format (step 807) so that sensor data of various formats is made readily usable by the applications within the grouping. For example, the controller 201 may create a universal video data format usable by all the applications that use video data. For another example, the controller 201 may determine a group of applications that are healthcare applications. The controller 201 may then create a standard, universal format readable by all the healthcare applications and convert received data of various types to the universal format. In doing so, the controller 201 expands the data usable by all the healthcare applications. In yet another example, the controller 201 may determine that a group of healthcare applications processes regulated healthcare data (versus unregulated data). Data may be regulated, for example, by the Health Insurance Portability and Accountability Act. Then, controller 201 may create a universal data format for transferring the data, whereas unregulated data may be stripped of user identity associations and transferred or used more freely.

Figure 9:
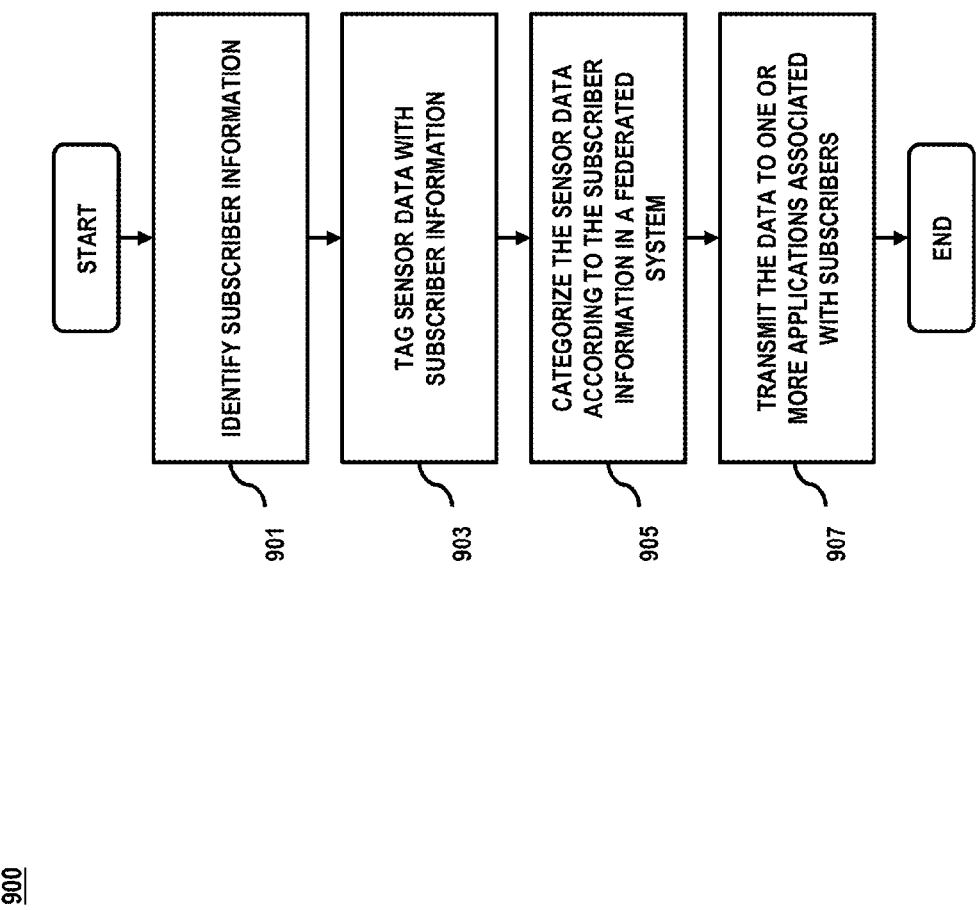
FIG. 9 is a flowchart of an end-to-end security process, according to one embodiment.

FIG. 9 is a flowchart of an end-to-end security assurance process described above which may be carried out by an embodiment illustrated in FIG. 2A, for example, to add security to the data transmitted by sensors. For steps 901 and 903, the controller 201 may determine subscriber information and tag sensor data with the subscriber information. For example, the subscriber information may include unique identifiers for the subscribers including identifiers for users, devices, members, or a combination thereof. The controller 201 may use the subscriber information to enhance security where access to the data is contingent on sources attempting to access the data showing that they have proper identifiers or authorization. For example, permitting access to the data may include universal identification mechanisms. Then, the controller 201 may categorize data according to the subscriber information (step 905).

In one embodiment, the data is stored in a federated system according to subscriber information such that users or applications can access data associated with the subscriber, regardless of user or subscriber location. For example where the subscriber is a user or device, data associated with the user or device may be accessible in the federated system via presentation of the user and device information. In this way, the controller 201 may always monitor data for a subscriber, regardless of the subscriber's location or service used. Then, the data may be tagged with subscriber information wherein access to the sensor data is based, at least in part, on the subscriber information. In one embodiment, the controller 201 may then transmit the data to applications associated with the subscribers (step 907). Furthermore, the controller 201 may determine the trends by processing the sensor data in conjunction with subscriber information. For example, sensor data may include blood pressure data. Subscriber information may be user profile information including a user's age, health history, family health history, and other body measurements. The controller 201 may then determine trends by analyzing the sensor blood pressure data while taking into account the subscriber's information. In a further embodiment, the controller 201 may determine registration information for published data feeds associated with the metadata. For example, the controller 201 may determine that the subscribers have registered for published data feeds, either of known or unknown origin. In this way, the controller 201 may receive new data as it becomes available.

Figure 10A:
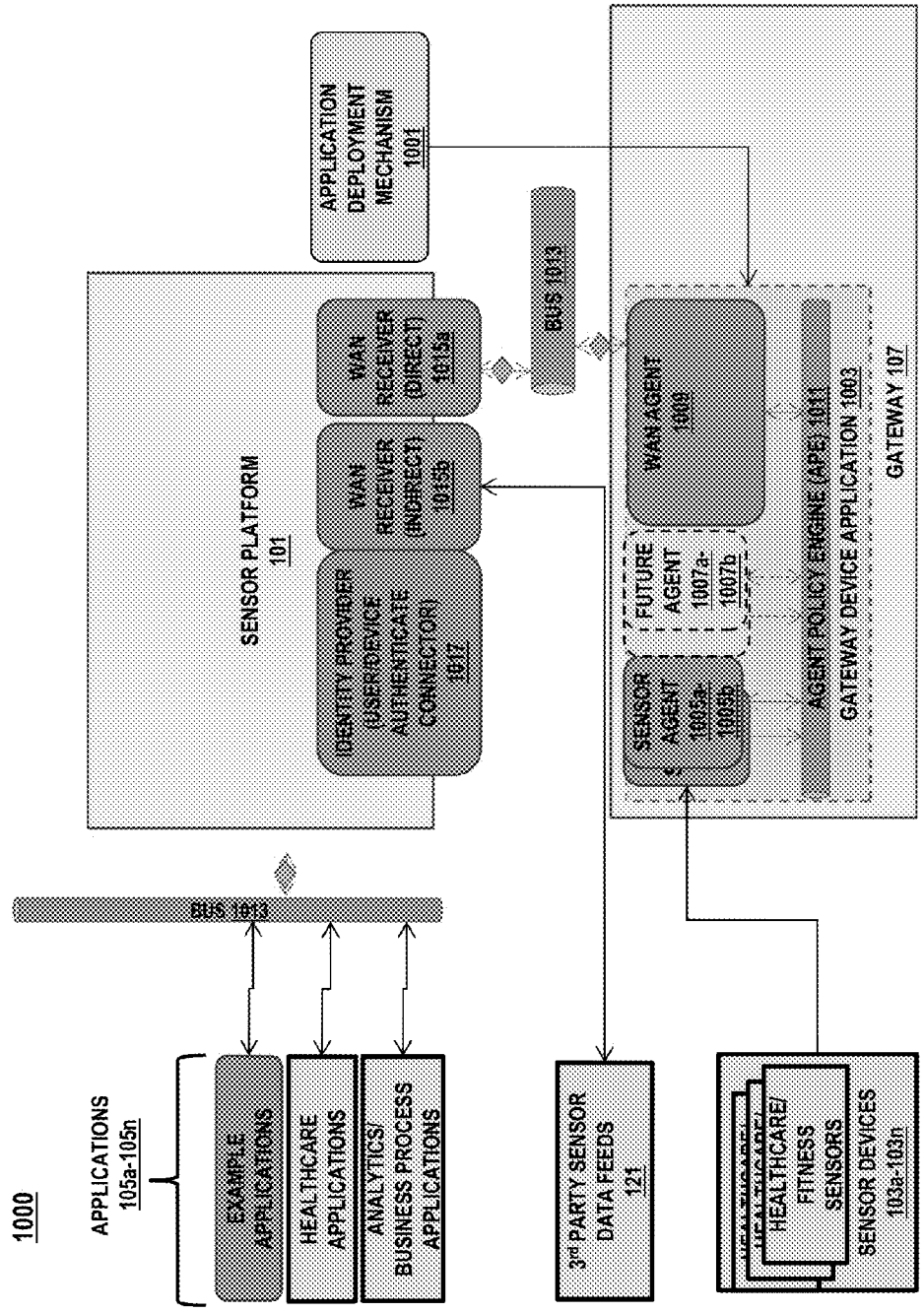
FIG. 10A is a diagram of a wireless environment where data from various sensors enters the sensor platform via a gateway, according to one embodiment.
Figure 10B:
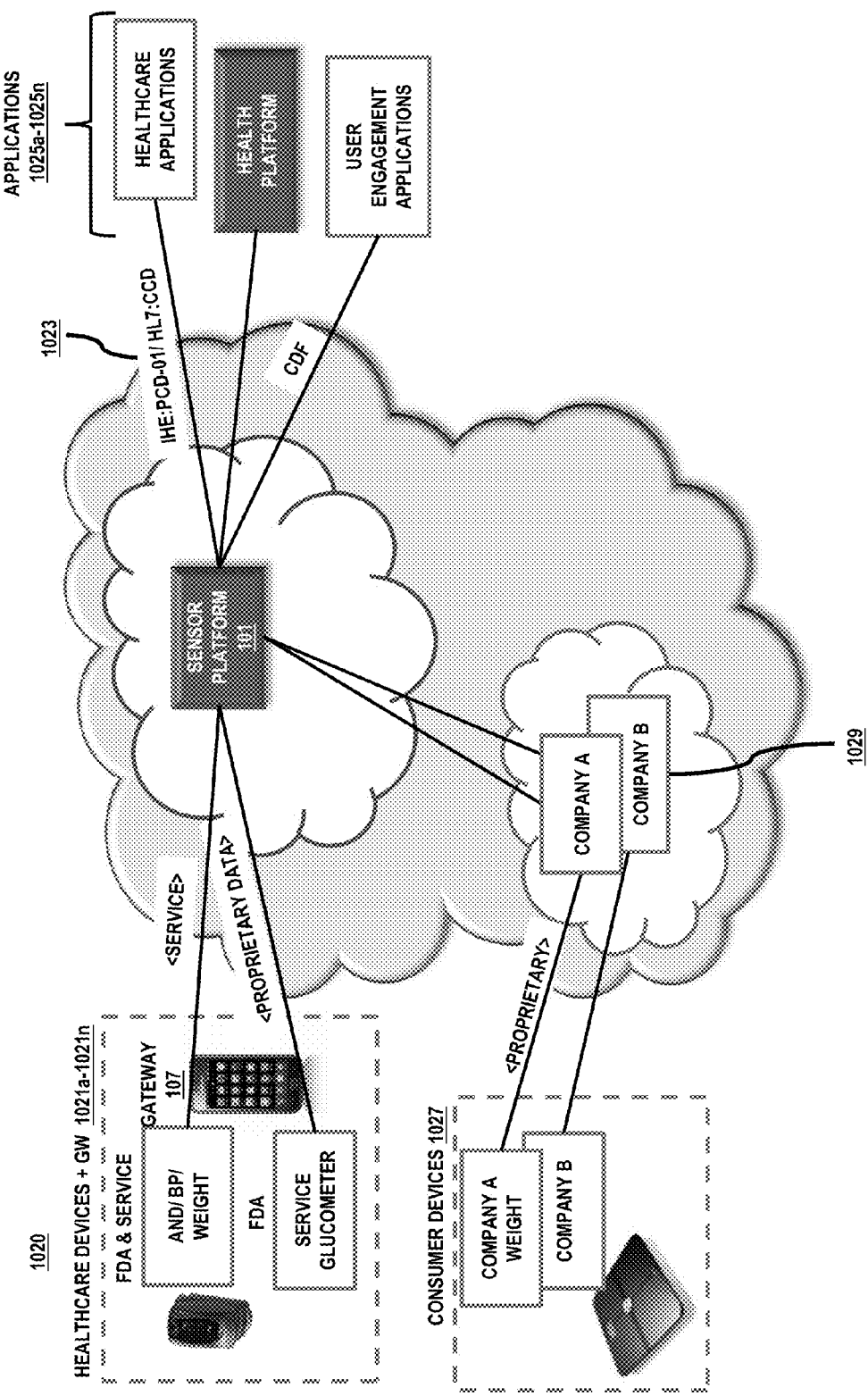
FIG. 10B is a diagram of a use case involving a system architecture for supporting health-related services, according to one embodiment.
Figure 10C:
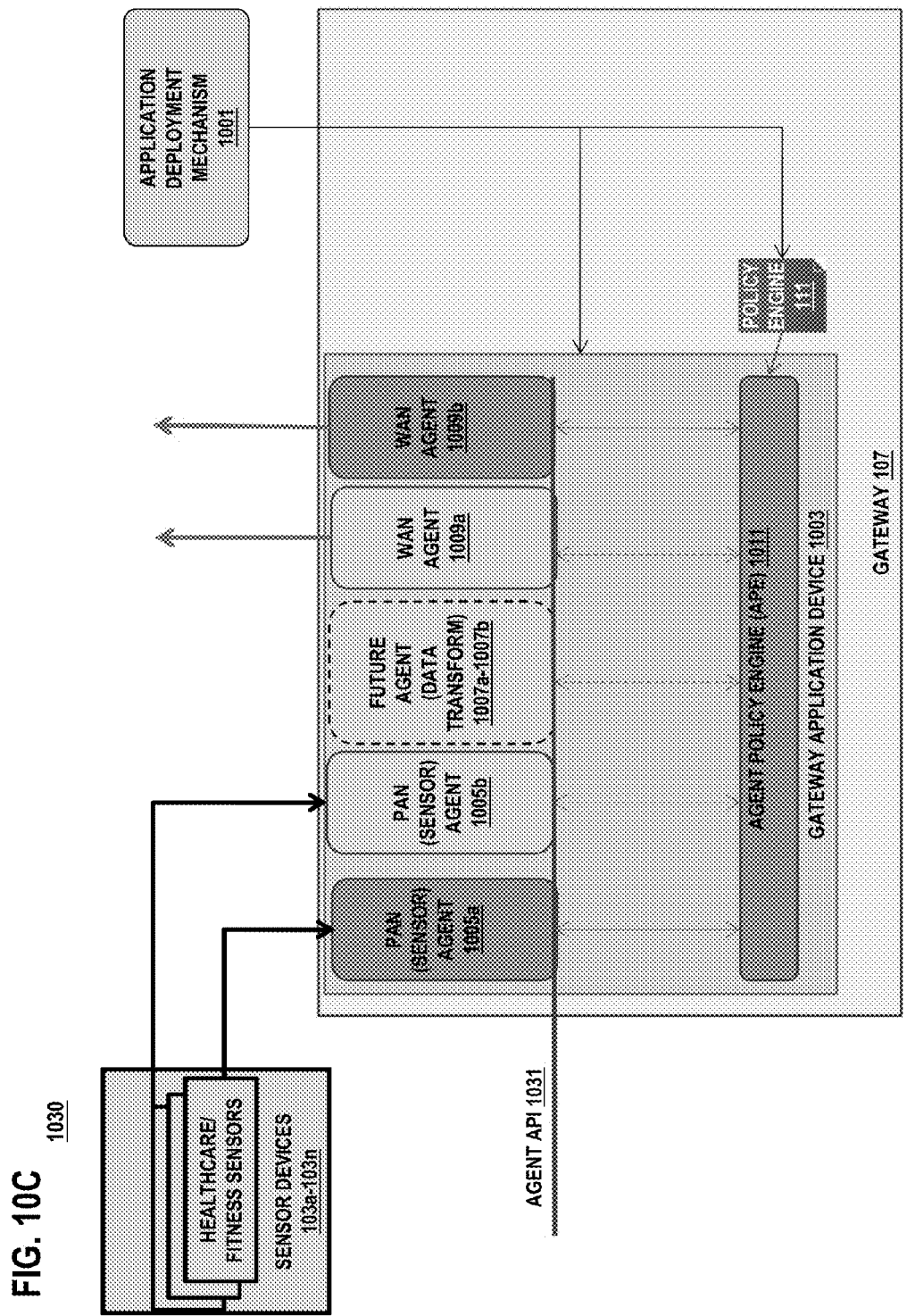
FIG. 10C is a diagram of a gateway device used in the system of FIG. 1, according to one embodiment.

FIGS. 10A-10C represent various illustrations of a wireless environment executing system 100. For example, FIG. 10A presents a broad overview of sensor devices interacting with the sensor platform 101. FIG. 10B illustrates a use case involving healthcare applications. FIG. 10C is a detailed diagram of the interactions conducted in gateway 107 similar to those employing a publisher-subscriber architecture.

FIG. 10A is a diagram of a wireless environment where data from various sensors enters the sensor platform via a gateway, according to one embodiment. According to one embodiment, sensors may include healthcare and fitness sensors which may communicate with one another through a PAN 109 in a gateway 107. The application deployment mechanism 1001 within the gateway 107 may automatically install the gateway device application 1003 onto the gateway 107. The application deployment mechanism 1001 may install and run a sensor platform gateway device application 1003 in the gateway 107. This sensor platform gateway device application 1003 may allow various sensor agents 1005a-1005b that transmit data from all the sensor devices 103 within the PAN 109 to communicate with one another and the sensor platform 101 in a unified and organized manner. The gateway device application 1003 also allows for the ability to plug in future sensor agents 1007a-1007b, and the ability to communicate with a WAN agent 1009. Each of these agents 1005-1009 are relatively autonomous and may have varying levels of communication with one another depending on their various policies. These policies contain the rules that dictate the levels of communication these agents 1005-1009 may have with one another. These various agents 1005-1009 may communicate with one another by way of the agent policy engine (APE) 1011. This APE 1011 is a pluggable bus-type system that functions as a chat room for all internetwork agents 1005-1009.

The APE 1011 may communicate the data that it receives from the sensor devices 103 into the sensor platform 101 through the WAN agent 1009. For example, the system 100 may employ a bus 1013 as the communication channel through which all of the information that comes in and out of the sensor platform 101 utilizes. In one instance, the bus 1013 may be an Extensive Messaging Presence Protocol (XMPP) bus. When the data is transmitted to the sensor platform 101 through a gateway device application's WAN agent 1009, the bus 1013 will receive this data and feed it into the direct WAN receiver 1015. When the bus 1013 receives data from a third party sensor feed 121, it will transmit this data to the sensor platform 101 through an indirect WAN receiver 1015b. Once at the sensor platform 101, the sensor platform 101 may perform a metrics analysis based, for example, on common data. Once the data reaches the sensor platform 101, it may be stored, converted to a new format, and or used to create analytics. Additionally, the sensor platform 101 may communicate the data into a plurality of applications 105 through the bus 1013. Examples of such applications 105 may include healthcare applications, analytics or business process applications, and others. The sensor platform 101 may also have an identity provider component 1017 which allows for user authentication. For example, universal identification systems may be one embodiment of an identity provider component 1017.

FIG. 10B is a diagram showing an overview of a wireless environment 1020 where data from various sensors enters the sensor platform 101 via the gateway. For example, sensors 1021a-1021n may connect with gateway 107 to interact with sensor platform 101. In other words, gateway 107 may automatically extract sensor data from sensors 1021a-1021n. In one scenario, the sensors 1021a-1021n may include healthcare-related sensors monitoring blood pressure, weight, blood glucose. The sensors 1021a-1021n may include both sensors that are compliant and sensors that are non-compliant with standards, such as governmental (e.g., Food and Drug Administration (FDA)) standards. Furthermore, sensors 1021a-1021n may include sensors certified by particular healthcare solution such that the sensors 1021a-1021n are vertically integrated with the sensor platform and applications associated with healthcare solution services.

Gateway 107 may be associated with one or more locations, users, locations associated with users, etc. For example, gateway 107 may be a mobile device belonging to a given user. For instance, user A's cell phone may act as a gateway 107, extracting and/or monitoring the blood pressure and weight of user A. The monitoring may be continuous or comprised of incremental measurements. In another example, gateway 107 may include a device designated as a "home gateway", where the gateway 107 provides a sensor contact point at user A's "Home." The system 100 may associate each gateway 107 with its own collection of sensors 1021a-1021n. By way of example the "home gateway device" may contain data tags or signatures that provide certain additional features that are available for the sensors or agents that are within the "home PAN." These tags allow the sensors to collect information that is normally associated with home activities such as for example sleeping or personal home care. This may include transient information that relates to home care providers such as identification tags and identification activities.

In one embodiment, the gateway 107 may include sensor agents that process the sensor data and encode the data with various levels of security or identification tags. For example, the gateway 107 may send, to the sensor platform 101, sensor data processed through the sensor agents, where the data is coded as proprietary data or data specific for the healthcare solution. In this way, the gateway 107 may permit data storage in the sensor platform 101 without compromising data security. In one embodiment, the sensor platform 101 may support various types of data formats. For example, the sensor platform 101 may permit regulated and unregulated data, wherein regulated data may include specific regulatory compliant data (e.g., Health Insurance Portability and Accountability Act (HIPAA)) and unregulated data may include all data. For instance, the sensor platform 101 may detach data from user identifications associated with the data so that the data is anonymous. Such operations may include data anonymization or other encryption techniques.

In one embodiment, the sensor platform 101 may also convert data into universal formats 1023 so that the data is more freely accessible by various applications 1025a-1025n. For example, the common or universal formats 1023 may be contingent on the formats compatible with applications 1025a-1025n. In one scenario, the sensor platform 101 may convert data into the Common Data Format (CDF) for applications that can interface with CDF. In another scenario, the sensor platform 101 may convert data into formats compatible with the Integrating the Healthcare Enterprise (IHE) and/or Health Level 7 (HL7) where applications relate to healthcare. In yet another scenario, the sensor platform 101 may create its own universal format 1023 depending on the needs of applications involved with system 100.

In one embodiment, the sensor platform 101 also receives data from third party sensor data feeds 1027. For example, the sensors 1021a-1021n may provide direct connections to the sensor platform 101 via registered gateway 107, whereas the third party sensor data feeds 911 may include indirect connections to the sensor platform 101. In one instance, the third party sensor data feed 1027 may not be associated with particular users or user devices. The third party sensor data feeds 1027 may include sensor data from, for example, consumer devices. The data for this type of case then, may be associated with a particular manufacturer, vendor, and/or company. For example, a Company A scale may transmit a third party sensor data feed 1027 to sensor platform 101. In one case, the third party sensor data feed 1027 may first transmit the third party sensor data feed 1027 to a third party sensor agent 1029 for processing prior to sending the data to the sensor platform 101. In another instance a particular vendor or manufacturer may supply a sensor that must be used within a defined time period that might represent a freshness sensor on a consumable product. The freshness data may be transported within the sensor platform 101, share the same data feed, and be coupled to the user identification. The sensor agent may detect an anomalous condition and prevent the dispensing or signal an alarm that can be acted upon within a smaller component of the sensor platform.

FIG. 10C is a diagram of a gateway device used in the system of FIG. 1. According to one embodiment, an application deployment mechanism 1001 may automatically install the gateway device application 1003 into the device gateway 107 and all of the sensor devices 103 within the PAN 109. This installation process takes place in the background and demands no user interaction. According to one embodiment, this application process occurs upon registration of the device. According to another embodiment, this installation process may automatically take place in the background when the new sensor device 103a is introduced into the PAN 109, networks 113-119, or WAN.

Each sensor device 103 in the PAN 109 may have a corresponding PAN sensor agent 1005a-1005b once the sensor devices 103 have the gateway device application 1003 installed. Each PAN sensor agent 1005a-1005b is relatively autonomous and may have a unique policy which details which of the other agents 1005-1009 in the gateway 107 it may publish or subscribe to, and the extent of the data within that publication or subscription. The PAN sensor agents 1005-1009 collect data from the sensor devices 103 and may engage in minor formatting conversions of the data. The WAN agent 1009a-1009b transmits data from the gateway 107 into the sensor platform 101. The agent API 1021 is how the PAN sensor agents 1005a-1005b and 1009a-1009b WAN sensor agents send data into the APE 1011. The APE 1011 is the communication venue for the various PAN sensor agents 1005a-1005b and WAN 1009a-1009b agents. The APE 1011 is a pluggable bus-type system which allows the agents 1005-1009 to publish their data while subscribing to the data of other agents 1005-1009. For example, a PAN sensor agent 1005a may publish data. A WAN agent 1009a may subscribe to the data published by the PAN sensor agent 1005a. The policy engine 111 contains all of the rules which determine the levels of communications, or publications and subscriptions, of each of the sensor agents 1005-1009. The policy engine 111 directs all of the communication that takes place among all of the autonomous sensor agents 1005-1009 within the APE 1011. The APE 1011 may accommodate future agents 1007a-1007b within its pluggable bus-type system, including those agents 1005-1009 that may require data conversions, due to the flexibility of the pluggable system.

The system components as described herein make the provisioning and commissioning of the sensors and other system components by various business entities, such as a fulfillment house, an integral part of the normal operation of data collection within the system. As such, the assignment or reassignment of a user to one or more users is accomplished as a form of data collection: this instance being the collection and association of trust between an end user and the sensor. An example of the data collection is described below.

Figure 11:
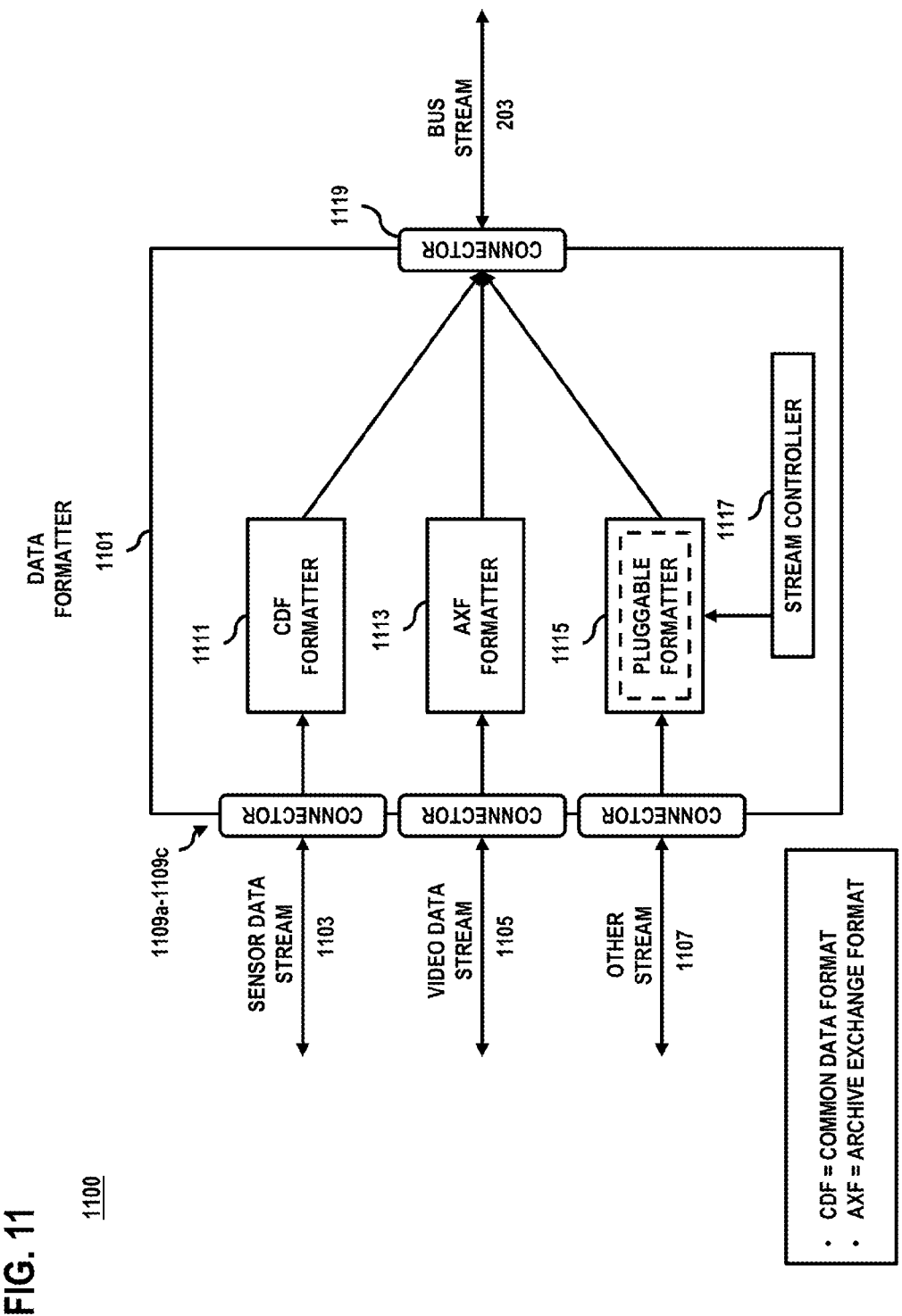
FIG. 11 is a diagram of an implementation of the data formatter of FIG. 3B, according to one embodiment.

FIG. 11 is a diagram of an implementation of the data formatter of FIG. 3B, according to one embodiment. According to one embodiment, the data formatter 1101 is a component within the sensor platform 101. This data formatter 1101 may have connector 1109 (or different connectors 1109a-1109c) for each data format. For example, there may be a connector 1109a for sensor data, another connector 1109b for video data, and so forth. There may also be connector 1109c that may be available for future sensor data formats. Each of these connectors 1109a-1109c may be linked to the formatter 1111-1115 capable of converting a particular type of format into a universal format. The connectors 1109 may correspond to the data format module 323 of FIG. 3B that determines the data format of incoming data. According to one embodiment, the connector 1109a which collects the sensor data stream 1103 may feed this data into the Common Data Format (CDF) formatter 1111 while the connector 1109b which collects a video data stream 1105 may feed this data into an Archive eXchange Format (AXF) 1113 formatter. Additionally, the connector 1109c that may be available for future data formats may feed data into a pluggable formatter 1115. Each of these formatters 1111-1115 may output the data into the same universal format. The formatters 1111-1115 may map to the universal format module 325, the selection module 327, and conversion module 329 shown in FIG. 3B, as they determine the format to which the data must be converted, and perform the conversion. The stream controller 1117 facilitates the transport of the converted data into the connector 1119 which feeds the bus 203 with data in a universal format. The bus 203 may communicate the universally formatted data to the various applications of the sensor platform 101.

Figure 12:
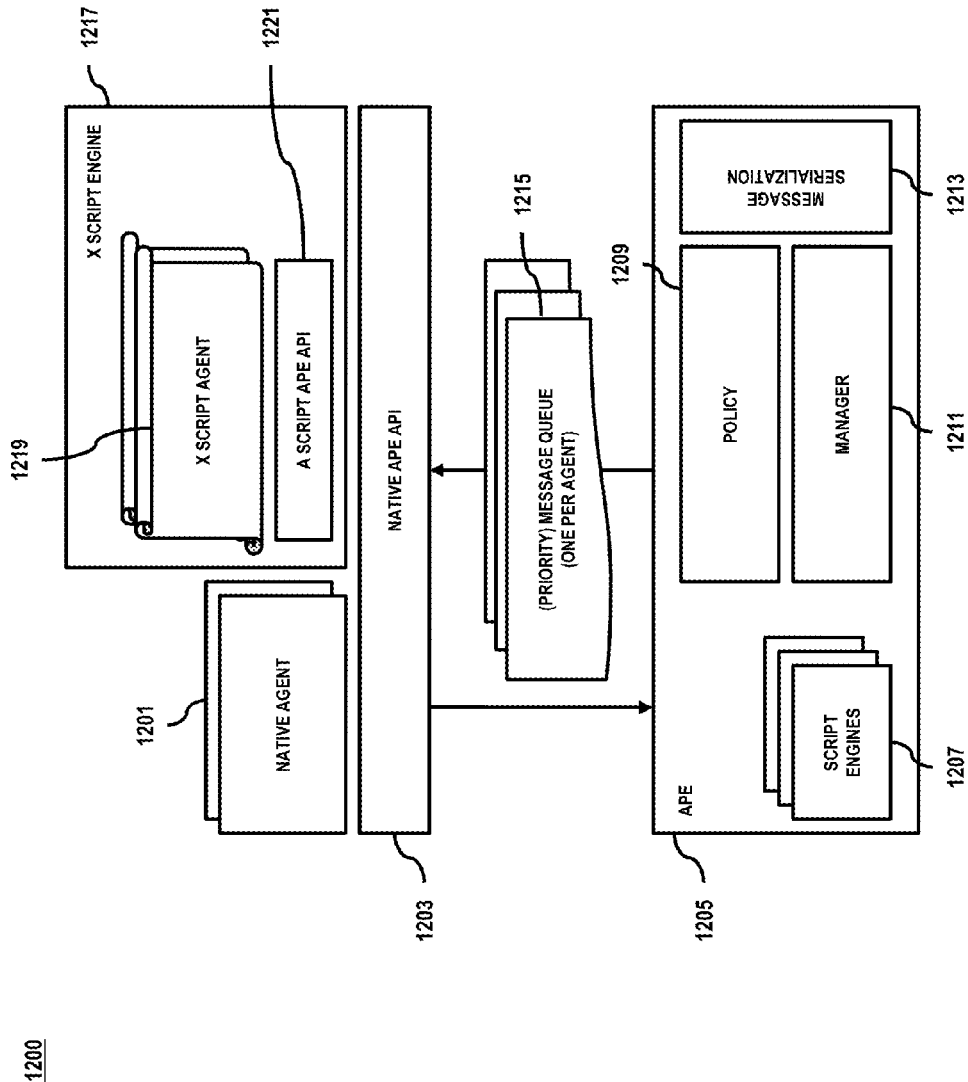
FIG. 12 is a diagram of a sensor agent development system, according to one embodiment.

FIG. 12 is a diagram of a sensor agent development system, according to one embodiment. In one embodiment, the sensor agents may include additional sensor agents, other than agents originally included or provided by the gateway, and/or third party sensor agents. The agent development system 1200 may be part of a gateway. In one embodiment, the system 1200 may include native agent 1201 already part of the gateway. The agent application programming interface (API) 1203 may provide a readily-accessible interface for all agents, where the API 1203 is in communication with an agent policy module 1205 that provides a pluggable "chat room" for the various agents. The agent policy module 1205 may include script engines 1207, policy 1209, manager 1211, and message serialization 1213. The script engines 1207 may support the communication between agents, the policy 1209 (as previously discussed) may offer the suite of access controls between agents, the manager 1211 may apply the access control terms or settings particular to each of the agents, while message serialization 1213 may convert data so that data may be transmitted for the communication. Message queue 1215 may manage the transmissions between agents and the agent policy module 1205.

Given this structure, the agent development system 1200 may include a script engine 1217 to facilitate the creation of new agents. In one embodiment, the script agent 1219 may include a script agent and script interface 1221. The script agent 1219 may include agent operations common to agents of the particular gateway. In this way, the script agent 1219 may automate or readily include execution of tasks that a new agent may require. Then, the script interface 1221 may make access to the native API 1203 readily available to further facilitate the process for agent developers in creating a new agent within a gateway or within system 100. In this way, the script engine 1217 automates the steps for agent creation such that developers are left with the single analysis performed by the agent, rather than needing to build the capability to interact with the rest of the gateway. The agent development system 1200 may also include a persistent message store 1223 to permit fast retrieval of messages to improve performance.

The processes described herein for machine-to-machine vertical integration may be implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

Figure 13:
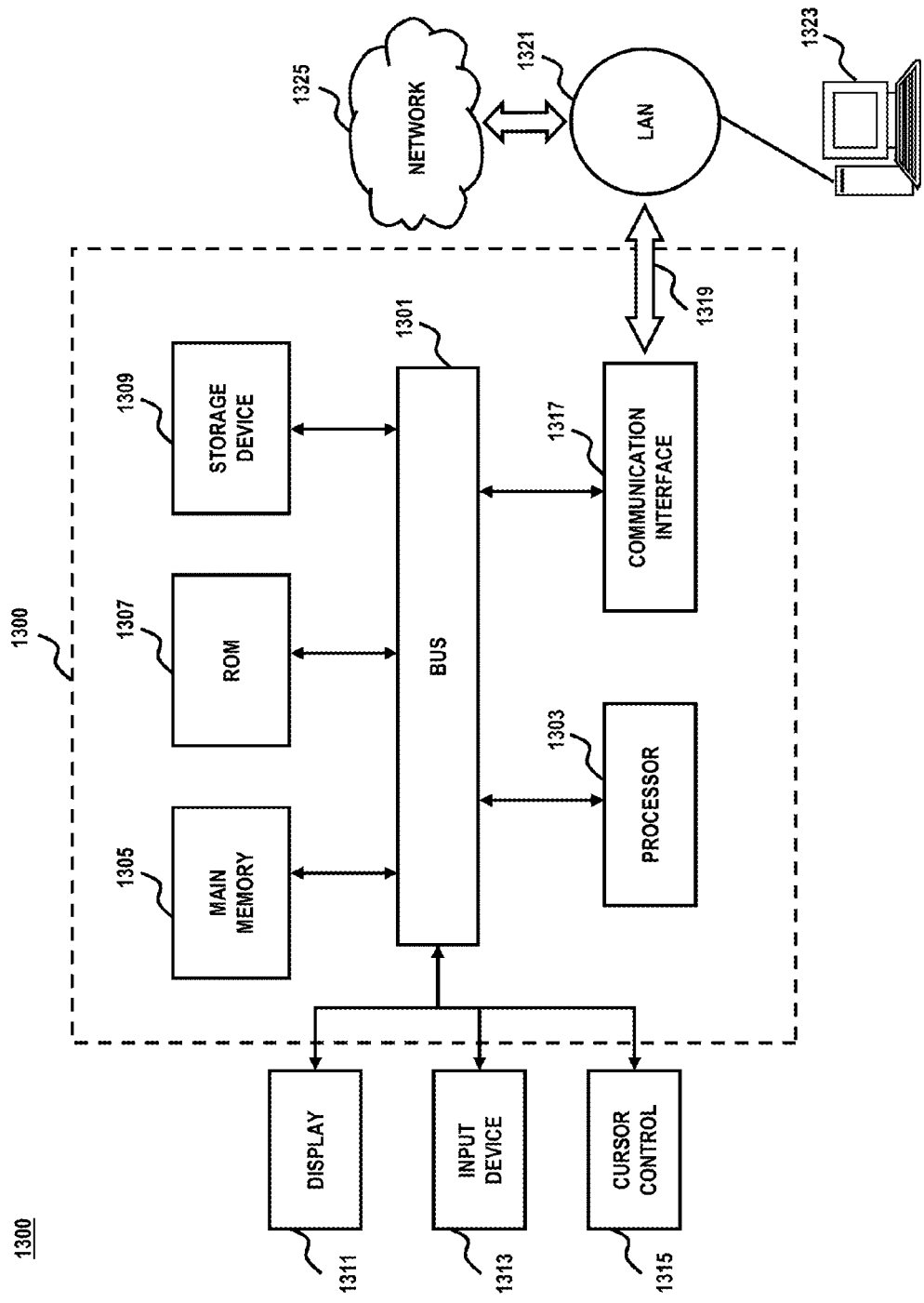
FIG. 13 is a diagram of a computer system that can be used to implement various exemplary embodiments.

FIG. 13 illustrates computing hardware (e.g., computer system) 1300 upon which exemplary embodiments can be implemented. The computer system 1300 includes a bus 1301 or other communication mechanism for communicating information and a processor 1303 coupled to the bus 1301 for processing information. The computer system 1300 also includes main memory 1305, such as a random access memory (RAM) or other dynamic storage device, coupled to the bus 1301 for storing information and instructions to be executed by the processor 1303. Main memory 1305 can also be used for storing temporary variables or other intermediate information during execution of instructions by the processor 1303. The computer system 1300 may further include a read only memory (ROM) 1307 or other static storage device coupled to the bus 1301 for storing static information and instructions for the processor 1303. A storage device 1309, such as a magnetic disk or optical disk, is coupled to the bus 1301 for persistently storing information and instructions.

The computer system 1300 may be coupled via the bus 1301 to a display 1311, such as a cathode ray tube (CRT), liquid crystal display, active matrix display, or plasma display, for displaying information to a computer user. An input device 1313, such as a keyboard including alphanumeric and other keys, is coupled to the bus 1301 for communicating information and command selections to the processor 1303. Another type of user input device is a cursor control 1315, such as a mouse, a trackball, or cursor direction keys, for communicating direction information and command selections to the processor 1303 and for controlling cursor movement on the display 1311.

According to an exemplary embodiment, the processes described herein are performed by the computer system 1300, in response to the processor 1303 executing an arrangement of instructions contained in main memory 1305. Such instructions can be read into main memory 1305 from another computer-readable medium, such as the storage device 1309. Execution of the arrangement of instructions contained in main memory 1305 causes the processor 1303 to perform the process steps described herein. One or more processors in a multi-processing arrangement may also be employed to execute the instructions contained in main memory 1305. In alternative embodiments, hard-wired circuitry may be used in place of or in combination with software instructions to implement exemplary embodiments. Thus, exemplary embodiments are not limited to any specific combination of hardware circuitry and software.

The computer system 1300 also includes a communication interface 1317 coupled to bus 1301. The communication interface 1317 provides a two-way data communication coupling to a network link 1319 connected to a local network 1321. For example, the communication interface 1317 may be a digital subscriber line (DSL) card or modem, an integrated services digital network (ISDN) card, a cable modem, a telephone modem, or any other communication interface to provide a data communication connection to a corresponding type of communication line. As another example, communication interface 1317 may be a local area network (LAN) card (e.g. for Ethernet™ or an Asynchronous Transfer Mode (ATM) network) to provide a data communication connection to a compatible LAN. Wireless links can also be implemented. In any such implementation, communication interface 1317 sends and receives electrical, electromagnetic, or optical signals that carry digital data streams representing various types of information. Further, the communication interface 1317 can include peripheral interface devices, such as a Universal Serial Bus (USB) interface, a PCMCIA (Personal Computer Memory Card International Association) interface, etc. Although a single communication interface 1317 is depicted in FIG. 13, multiple communication interfaces can also be employed.

The network link 1319 typically provides data communication through one or more networks to other data devices. For example, the network link 1319 may provide a connection through local network 1321 to a host computer 1323, which has connectivity to a network 1325 (e.g. a wide area network (WAN) or the global packet data communication network now commonly referred to as the "Internet") or to data equipment operated by a service provider. The local network 1321 and the network 1325 both use electrical, electromagnetic, or optical signals to convey information and instructions. The signals through the various networks and the signals on the network link 1319 and through the communication interface 1317, which communicate digital data with the computer system 1300, are exemplary forms of carrier waves bearing the information and instructions.

The computer system 1300 can send messages and receive data, including program code, through the network(s), the network link 1319, and the communication interface 1317. In the Internet example, a server (not shown) might transmit requested code belonging to an application program for implementing an exemplary embodiment through the network 1325, the local network 1321 and the communication interface 1317. The processor 1303 may execute the transmitted code while being received and/or store the code in the storage device 1309, or other non-volatile storage for later execution. In this manner, the computer system 1000 may obtain application code in the form of a carrier wave.

The term "computer-readable medium" as used herein refers to any medium that participates in providing instructions to the processor 1303 for execution. Such a medium may take many forms, including but not limited to non-volatile media, volatile media, and transmission media. Non-volatile media include, for example, optical or magnetic disks, such as the storage device 1309. Volatile media include dynamic memory, such as main memory 1305. Transmission media include coaxial cables, copper wire and fiber optics, including the wires that comprise the bus 1301. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read. In certain cases the computer readable media may include an unknown physical component wherein the information is uniquely defined by a special digital unique identifier and is available through multiple physical channels either simultaneously or exclusively.

Various forms of computer-readable media may be involved in providing instructions to a processor for execution. For example, the instructions for carrying out at least part of the exemplary embodiments may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

Figure 14:
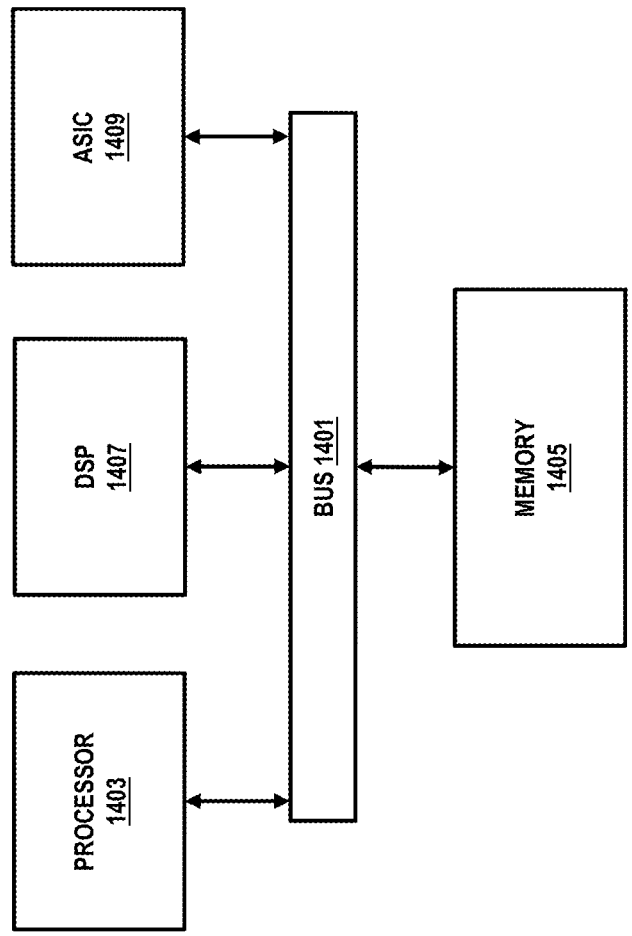
FIG. 14 is a diagram of a chip set upon which an embodiment of the invention may be implemented, according to one embodiment.

FIG. 14 illustrates a chip set 1400 upon which an embodiment of the invention may be implemented. Chip set 1400 is programmed to present a slideshow as described herein and includes, for instance, the processor and memory components described with respect to FIG. 10 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1400, or a portion thereof, constitutes a means for performing one or more steps of FIGS. 4-9.

In one embodiment, the chip set 1400 includes a communication mechanism such as a bus 1401 for passing information among the components of the chip set 1400. A processor 1403 has connectivity to the bus 1401 to execute instructions and process information stored in, for example, a memory 1405. The processor 1403 may include one or more processing cores with each core configured to perform independently. A multi-core processor enables multiprocessing within a single physical package. Examples of a multi-core processor include two, four, eight, or greater numbers of processing cores. Alternatively or in addition, the processor 1403 may include one or more microprocessors configured in tandem via the bus 1401 to enable independent execution of instructions, pipelining, and multithreading. The processor 1403 may also be accompanied with one or more specialized components to perform certain processing functions and tasks such as one or more digital signal processors (DSP) 1407, or one or more application-specific integrated circuits (ASIC) 1409. A DSP 1407 typically is configured to process real-world signals (e.g., sound) in real time independently of the processor 1403. Similarly, an ASIC 1409 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1403 and accompanying components have connectivity to the memory 1405 via the bus 1401. The memory 1405 includes both dynamic memory (e.g., RAM, magnetic disk, writable optical disk, etc.) and static memory (e.g., ROM, CD-ROM, etc.) for storing executable instructions that when executed perform the inventive steps described herein to controlling a set-top box based on device events. The memory 1405 also stores the data associated with or generated by the execution of the inventive steps.

While certain exemplary embodiments and implementations have been described herein, other embodiments and modifications will be apparent from this description. Accordingly, the invention is not limited to such embodiments, but rather to the broader scope of the presented claims and various obvious modifications and equivalent arrangements.

What is claimed is:

1. A method comprising:
    detecting a plurality of sensors associated with a plurality of subscribers,
        wherein the detecting includes identifying respective sensors in the plurality of sensors;
    dynamically registering, utilizing at least one processor, the respective sensors in the plurality of sensors, wherein registering the plurality of sensors includes installing interfacing software associated with one or more of the plurality of sensors;
creating at least two sensor agents associated with one or more of the registered sensors based on the identification;
determining one or more sensor agent policy settings,
wherein the determined sensor agent policy settings are configured to enhance data processing, via the at least two sensor agents, in delivering a limited selection of data originating from the detected plurality of sensors;
generating one or more connections between the at least two sensor agents;
monitoring the plurality of sensors to acquire raw sensor data associated with the plurality of subscribers;
acquiring the raw sensor data from the plurality of sensors, utilizing the at least two connected sensor agents, as a collective data set based on the sensor agent policy settings; and
converting, at least in part, the acquired raw sensor data into a universal format compatible with different types of applications,
wherein the collective data set includes converted data based on acquired raw sensor data.

2. The method of claim 1, further comprising:
identifying one or more trends in the sensor data utilizing the one or more sensor agents;
tagging the collective data set with metadata associated with the determined trends; and
creating analytics associated with the identified one or more trends,
wherein the plurality of sensors are direct sensors.

3. The method of claim 1, further comprising:
transmitting the converted data to two or more different types of applications.

4. The method of claim 3, further comprising:
detecting a data format associated with the acquired sensor data; and
creating the universal data format based on the detected data format.

5. The method of claim 3, further comprising:
determining one or more characteristics associated with the one or more applications associated with the collective data set;
grouping the applications based on the characteristics; and
creating the universal data format based on the application grouping.

6. The method of claim 1, further comprising:
determining subscriber information; and
tagging the acquired sensor data with the subscriber information,
wherein access to the collective data set is based, at least in part, on the tagged subscriber information.

7. The method of claim 1, wherein the subscribers include users, devices, gateways, services, or a combination thereof.

8. The method of claim 1, further comprising:
determining subscriber registration information associated with published data feeds.

9. An apparatus comprising:
at least one processor; and
at least one memory including computer program code for one or more programs,
the at least one memory and the computer program code configured to, with the at least one processor, cause the apparatus to perform at least the following,
detect a plurality of sensors associated with a plurality of subscribers,
wherein the detecting includes identifying respective sensors in the plurality of sensors,
dynamically register the respective sensors in the plurality of sensors,
wherein registering the plurality of sensors includes installing interfacing software associated with one or more of the plurality of sensors,
create at least two sensor agents associated with one or more of the registered sensors based on the identification,
determine one or more sensor agent policy settings,
wherein the determined sensor agent policy settings are configured to enhance data processing, via the at least two sensor agents, in delivering a limited selection of data originating from the detected plurality of sensors,
generate one or more connections between the at least two sensor agents,
monitor the plurality of sensors to acquire raw sensor data associated with the plurality of subscribers,
acquire the raw sensor data from the plurality of sensors, utilizing the at least two connected sensor agents, as a collective data set based on the sensor agent policy settings, and
convert, at least in part, the acquired raw sensor data into a universal format compatible with different types of applications,
wherein the collective data set includes converted data based on acquired raw sensor data.

10. The apparatus according to claim 9, wherein the apparatus is further caused to:
identify one or more trends in the sensor data utilizing the one or more sensor agents,
tag the collective data set with metadata associated with the determined trends, and
create analytics associated with the identified one or more trends,
wherein the plurality of sensors are direct sensors.

11. The apparatus according to claim 9, wherein the apparatus is further caused to:
transmit the converted data to two or more different types of applications.

12. The apparatus according to claim 11, wherein the apparatus is further caused to:
detect a data format associated with the acquired sensor data; and
create the universal data format based on the detected data format.

13. The apparatus according to claim 11, wherein the apparatus is further caused to:
determine one or more characteristics associated with the one or more applications associated with the collective data set;
group the applications based on the characteristics; and
create the universal data format based on the application grouping.

14. The apparatus according to claim 9, wherein the apparatus is further caused to:
determine subscriber information; and
tag the acquired sensor data with the subscriber information,
wherein access to the collective data set is based, at least in part, on the tagged subscriber information.

15. The apparatus according to claim 9, wherein the subscribers include users, devices, gateways, services, or a combination thereof.

16. The apparatus according to claim 9, wherein the apparatus is further caused to:
determine subscriber registration information associated with published data feeds.

17. A system comprising:
at least one processor;
a plurality of sensors associated with a plurality of subscribers; and
a sensor platform,
the sensor platform and the plurality of sensors configured to, with the at least one processor, cause the system to perform at least the following,
detect the plurality of sensors,
wherein the detecting includes identifying respective sensors in the plurality of sensors,
dynamically register the respective sensors in the plurality of sensors,
wherein registering the plurality of sensors includes installing interfacing software associated with one or more of the plurality of sensors,
create at least two sensor agents associated with one or more of the registered sensors based on the identification,
determine one or more sensor agent policy settings,
wherein the determined sensor agent policy settings are configured to enhance data processing, via the at least two sensor agents, in delivering a limited selection of data originating from the detected plurality of sensors,
generate one or more connections between the at least two sensor agents,
monitor the plurality of sensors to acquire raw sensor data associated with the plurality of subscribers,
acquire the raw sensor data from the plurality of sensors, utilizing the at least two connected sensor agents, as a collective data set based on the sensor agent policy settings, and
convert, at least in part, the acquired raw sensor data into a universal format compatible with different types of applications,
wherein the collective data set includes converted data based on acquired raw sensor data.

18. The system of claim 17, further configured to
identify one or more trends in the sensor data utilizing the one or more sensor agents,
tag the collective data set with metadata associated with the determined trends, and
create analytics associated with the identified one or more trends,
wherein the plurality of sensors are direct sensors.

19. The system of claim 17, further configured to
convert the sensor data into a universal data format; and
transmit the converted data to two or more different types of applications.

20. The system of claim 19, further configured to
detect a data format associated with the acquired sensor data; and
create the universal data format based on the detected data format.

21. The system of claim 19, further configured to
determine one or more characteristics associated with the one or more applications associated with the collective data set;
group the applications based on the characteristics; and
create the universal data format based on the application grouping.

22. The system of claim 17, further configured to:
determine subscriber information; and
tag the acquired sensor data with the subscriber information,
wherein access to the collective data set is based, at least in part, on the tagged subscriber information.

23. The system of claim 17, wherein the subscribers include users, devices, gateways, services, or a combination thereof.

24. The system of claim 17, further configured to:
determine subscriber registration information associated with published data feeds.

* * * * *